(12) United States Patent
Miyakoshi et al.

(10) Patent No.: US 10,640,573 B2
(45) Date of Patent: May 5, 2020

(54) HUMAN ANTIBODY AGAINST AGGRECANASE-TYPE ADAMTS SPECIES FOR THERAPEUTICS OF AGGRECANASE-RELATED DISEASES

(71) Applicants: KEIO UNIVERSITY, Tokyo (JP); GeneFrontier Corporation, Kashiwa (JP)

(72) Inventors: Akira Miyakoshi, Kashiwa (JP); Mikiko Nakamura, Kashiwa (JP); Kanehisa Kojoh, Kashiwa (JP); Satsuki Mochizuki, Tokyo (JP); Yasunori Okada, Tokyo (JP)

(73) Assignees: GeneFrontier Corporation, Kashiwa-shi, Chiba (JP); Keio University, Tokyo (JP)

(*) Notice: Subject to any disclaimer, the term of this patent is extended or adjusted under 35 U.S.C. 154(b) by 0 days.

(21) Appl. No.: 16/153,413

(22) Filed: Oct. 5, 2018

(65) Prior Publication Data
US 2019/0233541 A1    Aug. 1, 2019

Related U.S. Application Data

(63) Continuation of application No. 15/029,823, filed as application No. PCT/JP2014/077767 on Oct. 14, 2014, now abandoned.

(60) Provisional application No. 61/891,087, filed on Oct. 15, 2013.

(51) Int. Cl.
| | |
|---|---|
| *C07K 16/00* | (2006.01) |
| *C07K 16/46* | (2006.01) |
| *A61K 39/395* | (2006.01) |
| *C07K 16/40* | (2006.01) |

(52) U.S. Cl.
CPC .......... *C07K 16/40* (2013.01); *C07K 2317/21* (2013.01); *C07K 2317/33* (2013.01); *C07K 2317/34* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2006/0228354 A1    10/2006    Corcoran et al.

FOREIGN PATENT DOCUMENTS

| JP | 2004-244339 A | 9/2004 |
|---|---|---|
| WO | WO 2011/002968 A2 | 1/2011 |
| WO | WO 2013/109829 A1 | 7/2013 |

OTHER PUBLICATIONS

Chiusaroli et al., "Targeting of ADAMTS5's ancillary domain with the recombinant mAb CRB0017 ameliorates disease progression in a spontaneous murine model of osteoarthritis," *Osteoarthritis and Cartilage*, 21(11): 1807-1810 (2013).
Fosang et al., "ADAMTS-5: The Story So Far," *European Cells and Materials*, 15: 11-26 (2008).
Glasson et al., "Deletion of active ADAMTS5 prevents cartilage degradation in a murine model of osteoarthritis," *Nature*, 434(7033): 644-648 (2005).
Hashimoto et al., "Inhibition of ADAMTS4 (aggrecanase-1) by tissue inhibitors of metalloproteinases (TIMP-1, 2, 3, and 4)," *FEBS Letters*, 494(3): 192-195 (2001).
Hashimoto et al., "ADAMTS4 (Aggrecanase-1) Interaction with the C-terminal Domain of Fibronectin Inhibits Proteolysis of Aggrecan," *The Journal of Biological Chemistry*, 279(31): 32483-32491 (2004).
Heinegard, "Proteoglycans and more—from molecules to biology," *International Journal of Experimental Pathology*, 90(6): 575-586 (2009).
Larkin et al., "Translational development of an ADAMTS-5 antibody for osteoarthritis disease modification," *Osteoarthritis and Cartilage*, 23(8): 1254-1266 (2015).
Murphy, "The ADAMs: signalling scissors in the tumour microenvironment," *Nature Reviews Cancer*, 8(12): 929-941 (2008).
Naito et al., "Expression of ADAMTS4 (aggrecanase-1) in human osteoarthritic cartilage," *Pathology International*, 57(11): 703-711 (2007).
Okada, "Proteinases and Matrix Degradation" (Chapter 8 at pp. 97-115) in *Kelly's Textbook of Rheumatology*, 9th edition, edited by Firestein et al., Elsevier Saunders, Philadelphia, USA (2013).
Pratta et al., "Aggrecan Protects Cartilage Collagen from Proteolytic Cleavage," *The Journal of Biological Chemistry*, 278(46): 45539-45545 (2003).
Shiomi et al., "Matrix metalloproteinases, a disintegrin and metalloproteinases, and a disintegrin and metalloproteinases with thrombospondin motifs in non-neoplastic diseases," *Pathology International*, 60(7): 477-496 (2010).
Shiraishi et al., "Development of human neutralizing antibody to ADAMTS4 (aggrecanase-1) and ADAMTS5 (aggrecanase-2)," *Biochemical and Biophysical Research Communications*, 469(1): 62-69 (2016).
Stanton et al., "ADAMTS5 is the major aggrecanase in mouse cartilage in vivo and in vitro," *Nature*, 434(7033): 648-652 (2005).
Steidl et al., "In vitro affinity maturation of human GM-CSF antibodies by targeted CDR-diversification," *Mol. Immunol.*, 46(1): 135-144 (2008).
Takizawa et al., "Calcium pentosan polysulfate directly inhibits enzymatic activity of ADAMTS4 (aggrecanase-1) in osteoarthritic chondrocytes," *FEBS Letters*, 582(19): 2945-2949 (2008).

(Continued)

Primary Examiner — Maher M Haddad
(74) Attorney, Agent, or Firm — Osha Liang LLP

(57) ABSTRACT

The present invention provides an antibody that specifically binds to human aggrecanase, and inhibits enzymatic activity of the human aggrecanase. In one embodiment, aggrecanase is ADAMTS4. In one embodiment, the antibody recognizes a particular epitope in human ADAMTS4, and inhibits not only aggrecanase activity of human ADAMTS4 but also aggrecanase activity of human ADAMTS5. In addition, the present invention also provides use of said antibody in the prophylaxis or treatment of the progression of arthritis.

7 Claims, 4 Drawing Sheets
Specification includes a Sequence Listing.

(56) References Cited

OTHER PUBLICATIONS

Yamanishi et al., "Expression and Regulation of Aggrecanase in Arthritis: The Role of TGF-β," *The Journal of Immunology,* 168(3): 1405-1412 (2002).
Yatabe et al., "Hyaluronan inhibits expression of ADAMTS4 (aggrecanase-1) in human osteoarthritic chondrocytes," *Annals of the Rheumatic Diseases,* 68(6): 1051-1058 (2009).
Japanese Patent Office, International Search Report and Written Opinion of the International Searching Authority in International Patent Application No. PCT/JP2014/077767 (dated Dec. 2, 2014).
U.S. Appl. No. 15/029,823, filed Apr. 15, 2016, Pending.

A

B

HUMAN ANTIBODY AGAINST AGGRECANASE-TYPE ADAMTS SPECIES FOR THERAPEUTICS OF AGGRECANASE-RELATED DISEASES

CROSS-REFERENCE TO RELATED APPLICATIONS

This patent application is a continuation of copending U.S. patent application Ser. No. 15/029,823, filed on Apr. 15, 2016, which is the U.S. national phase of International Patent Application No. PCT/JP2014/077767, filed on Oct. 14, 2014, which claims the benefit of U.S. Provisional Patent Application No. 61/891,087, filed on Oct. 15, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 47,653 bytes ASCII (Text) file named "740833SequenceListing.txt," created Oct. 5, 2018.

TECHNICAL FIELD

The present invention relates to an anti-human aggrecanase antibody, and pharmaceutical use thereof.

BACKGROUND ART

Aggrecan degradation and subsequent digestion of collagen fibrils are the central pathway for the destruction of cartilage in human joint diseases including osteoarthritis (OA) and rheumatoid arthritis (RA). Collagen degradation is carried out principally by collagen-degrading matrix metalloproteinases (MMPs) such as MMP-1, MMP-8 and MMP-13 [1-3]. On the other hand, aggrecan-degrading metalloproteinases called aggrecanases are considered to play a key role in the aggrecan degradation [4, 5]. Aggrecanases belong to the ADAMTS (a disintegrin and metalloproteinase with thrombospondin motifs) gene family, and ADAMTS1, 4, 5, 8, 9 and 15 are known to have aggrecanase activity [4, 6]. Recent studies using ADAMTS4 and ADAMTS5 knockout mice have indicated that ADAMTS5, but not ADAMTS4, plays an essential role in aggrecan degradation in mouse arthritides [7, 8]. However, because there is little information about the biochemical character, expression patterns or gene promoter structures of mouse ADAMTS4 and ADAMTS5, the data from knockout mice must be interpreted carefully and should not be extrapolated to the human disease OA and RA [9, 10]. In human chondrocytes, ADAMTS4 is inducible by treatment with cytokines such as interleukin-1 (IL-1), but the expression of ADAMTS5 is constitutive [9, 11-13]. Our recent study also showed that among aggrecanase-type ADAMTS species, ADAMTS4 is selectively overexpressed in human osteoarthritic cartilage with a direct correlation to the degree of cartilage destruction, while ADAMTS5 is constitutively expressed in both normal and osteoarthritic cartilage [10]. These suggest that ADAMTS4 is a major aggrecanase in human osteoarthritic cartilage. ADAMTS4 is also overexpressed by synovial cells and articular chondrocytes in RA, suggesting the involvement of this proteinase in cartilage destruction of RA joints. ADAMTS4 and ADAMTS5 can digest not only aggrecan but also other members of the proteoglycan lectican family including versican and brevican. Since versican is a major proteoglycan in the skin and blood vessel wall, its degradation by ADAMTS4 and ADAMTS5 is also implicated in tissue destruction and repair of the skin and blood vessels under pathological conditions such as chronic ulcer and fibrosis of the skin and various vasculitides, respectively. In addition, tumor cells in glioblastoma multiforme are known to overexpress ADAMTS5 and tumor cell-derived ADAMTS5 is suggested to play a role in invasion by cleavage of brevican [14].

The phage display method is one of the display techniques that have realized an in vitro high-speed selection by forming a one-to-one correspondence in the form of phage particle between a functional peptide or protein and a DNA encoding same. This phage display method is applied to antibody selection, and many antibodies obtained by this method have been developed as pharmaceutical products [15]. Furthermore, a method of obtaining a specific antibody by a combination of a human artificial antibody library and a phage display method has been established, and such methods have been practicalized by plural companies, as evidenced by HuCAL (Human Combinatorial Antibody Library) of MorphoSys.

DOCUMENT LIST

Non-Patent Documents

[1] Dahlberg L, Billinghurst R C, Manner P, Nelson F, Webb G, Ionescu M, et al. Selective enhancement of collagenase-mediated cleavage of resident type II collagen in cultured osteoarthritic cartilage and arrest with a synthetic inhibitor that spares collagenase 1 (matrix metalloproteinase 1). Arthritis Rheum. 2000; 43: 673-82.

[2] Tortorella M D, Malfait A M, Deccico C, Arner E. The role of ADAM-TS4 (aggrecanase-1) and ADAM-TS5 (aggrecanase-2) in a model of cartilage degradation. Osteoarthritis Cartilage. 2001; 9: 539-52.

[3] Pratta M A, Yao W, Decicco C, Tortorella M D, Liu R Q, Copeland R A, et al. Aggrecan protects cartilage collagen from proteolytic cleavage. J Biol Chem. 2003; 278: 45539-45.

[4] Porter S, Clark I M, Kevorkian L, Edwards D R. The ADAMTS metalloproteinases. Biochem J. 2005; 386: 15-27.

[5] Struglics A, Larsson S, Pratta M A, Kumar S, Lark M W, Lohmander L S. Human osteoarthritis synovial fluid and joint cartilage contain both aggrecanase- and matrix metalloproteinase-generated aggrecan fragments. Osteoarthritis Cartilage. 2006; 14:101-13.

[6] Okada Y. Proteinases and matrix degradation. In: J Harris E D, Budd R C, Genovese M C, Firestein G S and Sargent J S (ed) Kelley's textbook of Rheumatology Philadelphia: 8th edition, Elsevier Saunders 2008, in press.

[7] Glasson S S, Askew R, Sheppard B, Carito B, Blanchet T, Ma H L, et al. Deletion of active ADAMTS5 prevents cartilage degradation in a murine model of osteoarthritis. Nature. 2005; 434: 644-8.

[8] Stanton H, Rogerson F M, East C J, Golub S B, Lawlor K E, Meeker C T, et al. ADAMTS5 is the major aggrecanase in mouse cartilage in vivo and in vitro. Nature. 2005; 434: 648-52.

[9] Song R H, Tortorella M D, Malfait A M, Alston J T, Yang Z, Arner E C, et al. Aggrecan degradation in human articular cartilage explants is mediated by both ADAMTS-4 and ADAMTS-5. Arthritis Rheum. 2007; 56: 575-85.

[10] Naito S, Shiomi T, Okada A, Kimura T, Chijiiwa M, Fujita Y, et al. Expression of ADAMTS4 (aggrecanase-1) in human osteoarthritic cartilage. Pathol Int. 2007; 57: 703-11.
[11] Bau B, Gebhard P M, Haag J, Knorr T, Bartnik E, Aigner T. Relative messenger RNA expression profiling of collagenases and aggrecanases in human articular chondrocytes in vivo and in vitro. Arthritis Rheum. 2002; 46: 2648-57.
[12] Moulharat N, Lesur C, Thomas M, Rolland-Valognes G, Pastoureau P, Anract P, et al. Effects of transforming growth factor-beta on aggrecanase production and proteoglycans degradation by human chondrocytes in vitro. Osteoarthritis Cartilage. 2004; 12: 296-305.
[13] Hui W, Barksby E, Young D A, Cawston T E, McKie N, Rowan A D. Oncostatin M in combination with tumour necrosis factor alpha induces a chondrocyte membrane-associated aggrecanase that is distinct from ADAMTS aggrecanase-1 or -2. Ann Rheum Dis. 2005; 64: 1624-32.
[14] Nakada M, Miyamori H, Kita D, Takahashi T, Yamashita J, Sato H, Miura R, Yamaguchi Y, Okada Y. Acta Neuropathol 110:239-246, 2005
[15] Rothe, C. et al. J. Mol. Biol. 2008; 376:1182-1200

SUMMARY OF INVENTION

Technical Problem

An object of the present invention is to provide an anti-human aggrecanase antibody (particularly, anti-human ADAMTS4 antibody) useful for the prophylaxis or treatment of the progression of various diseases represented by arthritis wherein Lectican family molecule, which is a proteoglycan, is degraded.

Solution to Problem

To solve the above-mentioned problem, the present inventors produced plural anti-human aggrecanase antibodies that bind to human aggrecanase. As a result, they have found that the produced anti-human ADAMTS4 antibodies inhibit enzymatic activity of human ADAMTS4, and can prevent aggrecan degradation by articular chondrocytes that occurs in arthritis. Furthermore, they have found that an antibody that recognizes a particular epitope also shows cross-reactivity with aggrecanases other than human ADAMTS4, and can also inhibit their activity. Based on the above-mentioned findings, they have conducted further studies in an attempt to develop a therapeutic drug for the diseases represented by arthritis, wherein aggrecanase acts on the tissue destruction, which resulted in the completion of the present invention.

Accordingly, the present invention relates to the following.
[1] An antibody which specifically binds to a human aggrecanase and inhibits aggrecanase activity of said aggrecanase.
[2] The antibody according to [1], wherein the human aggrecanase is human ADAMTS4.
[3] The antibody according to [2], which further inhibits aggrecanase activity of human ADAMTS5.
[4] The antibody according to [2] or [3], which binds to human ADAMTS4 at an epitope comprising the amino acid sequence depicted in SEQ ID NO: 9.
[5] The antibody according to any one of [2] to [4], which comprises a light chain variable region and a heavy chain variable region, wherein
(1) the light chain variable region comprises CDR1 comprising the amino acid sequence depicted in SEQ ID NO: 1, CDR2 comprising the amino acid sequence depicted in SEQ ID NO: 2 and CDR3 comprising the amino acid sequence depicted in SEQ ID NO: 3, and
the heavy chain variable region comprises CDR1 comprising the amino acid sequence depicted in SEQ ID NO: 4, CDR2 comprising the amino acid sequence depicted in SEQ ID NO: 5 and CDR3 comprising the amino acid sequence depicted in SEQ ID NO: 6; or
(2) the light chain variable region comprises CDR1 comprising the amino acid sequence depicted in SEQ ID NO: 1, CDR2 comprising the amino acid sequence depicted in SEQ ID NO: 2 and CDR3 comprising the amino acid sequence depicted in SEQ ID NO: 3, and
the heavy chain variable region comprises CDR1 comprising the amino acid sequence depicted in SEQ ID NO: 4, CDR2 comprising the amino acid sequence depicted in SEQ ID NO: 5 and CDR3 comprising the amino acid sequence depicted in SEQ ID NO: 6, except that 1 to 3 amino acids are substituted, deleted, inserted, or added in at least one amino acid sequence selected from the group consisting of SEQ ID NO: 1 to 3, and/or 1 to 3 amino acids are substituted, deleted, inserted, or added in at least one amino acid sequence selected from the group consisting of SEQ ID NO: 4 to 6.
[6] The antibody according to [5], wherein the light chain variable region comprises the amino acid sequence depicted in SEQ ID NO: 7 and the heavy chain variable region comprises the amino acid sequence depicted in SEQ ID NO: 8.
[7] The antibody according to any one of [1] to [6], which is a human antibody.
[8] A pharmaceutical composition which comprises the antibody according to any one of [1] to [7].
[9] A polynucleotide which encodes the antibody according to any one of [1] to [7].
[10] A vector which comprises the polynucleotide according to [9].
[11] A transformant which comprises the vector according to [10].
[12] An agent for preventing or treating arthritis, which comprises an antibody which specifically binds to a human aggrecanase and inhibits aggrecanase activity of said aggrecanase.
[13] The agent according to [12], wherein the human aggrecanase is human ADAMTS4.
[14] The agent according to [12] or [13], wherein the antibody is the antibody according to any one of [1] to [7].
[15] A method of preventing or treating arthritis in a mammal, which comprises administering effective amount of an antibody which specifically binds to a human aggrecanase and inhibits aggrecanase activity of said aggrecanase to the mammal.
[16] The method according to [15], wherein the human aggrecanase is human ADAMTS4.
[17] The method according to [15] or [16], wherein the antibody is the antibody according to any one of [1] to [7].
[18] An antibody which specifically binds to a human aggrecanase and inhibits aggrecanase activity of said aggrecanase, for use in prophylaxis or treatment of arthritis.
[19] The antibody according to [18], wherein the human aggrecanase is human ADAMTS4.
[20] The antibody according to [18] or [19], which is the antibody according to any one of [1] to [7].
[21] Use of an antibody which specifically binds to a human aggrecanase and inhibits aggrecanase activity of said aggrecanase, for producing an agent for preventing or treating arthritis.

[22] The use according to [21], wherein the human aggrecanase is human ADAMTS4.

[23] The use according to [21] or [22], wherein the antibody is the antibody according to any one of [1] to [7].

Advantageous Effect of Invention

According to the present invention, an anti-human aggrecanase antibody (particularly, anti-human ADAMTS4 antibody) useful for the prophylaxis or treatment of the progression of arthritis is provided.

DESCRIPTION OF EMBODIMENTS

Figure 1:
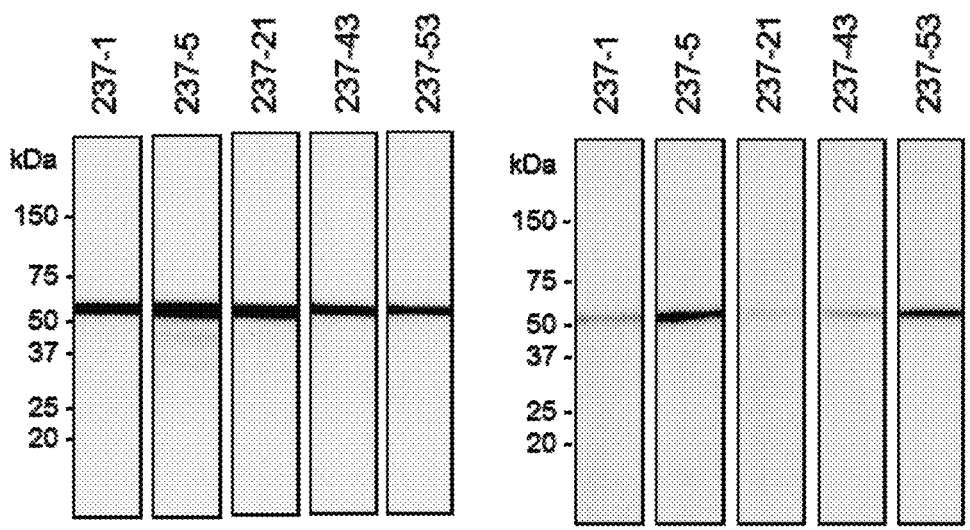
FIG. 1. Immunoreactivity of candidate Fabs with ADAMTS4 and ADAMTS5, and their inhibition of ADAMTS4 aggrecanase activity. (A) Recombinant ADAMTS4 (left) and ADAMTS5 (right) (100 ng/lane each) transferred onto the PVDF membranes were reacted with each candidate Fab (clone 237-1, 237-5, 237-21, 237-43 or 237-53), followed by immunoblotting. (B) Inhibition of ADAMTS4 activity by the Fabs. Recombinant ADAMTS4 (180 ng) was reacted with each Fab (clone 237-1, 237-5, 237-21, 237-43 or 237-53) or control Fab in a 1:1 molar ratio, and then incubated with aggrecan (100 μg) for 16 h at 37° C. Aggrecanase activity of ADAMTS4 was evaluated by immunoblotting with anti-aggrecan neoepitope (NITEGE$^{392}$) antibody. TS(−), buffer alone; Fab(−), ADAMTS4 incubated without Fab; Control, control Fab.
Figure 1:
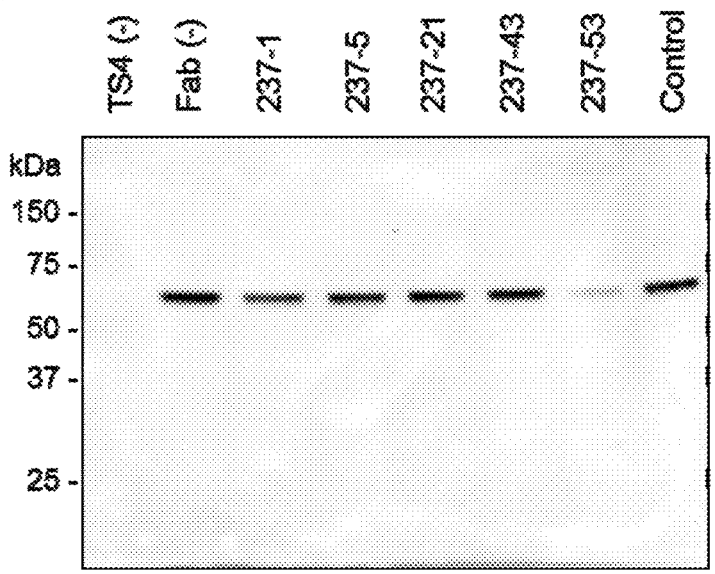

The present invention provides an antibody which has a specific binding activity to human aggrecanase, and inhibits the aggrecanase activity of the aggrecanase.

Aggrecanase is a known protease which is a member of the ADAMTS (a disintegrin and metalloproteinase with thrombospondin motifs) protein family, and acts on and degrades a proteoglycan known as aggrecan. Aggrecanase encompasses ADAMTS4, ADAMTS5, ADAMTS1, ADAMTS8, ADAMTS9, ADAMTS15 and the like.

A representative amino acid sequence of human ADAMTS4 is shown in SEQ ID NO: 15, a representative cDNA sequence of human ADAMTS4 is shown in SEQ ID NO: 14, a representative amino acid sequence of human ADAMTS5 is shown in SEQ ID NO: 17, and a representative cDNA sequence of human ADAMTS5 is shown in SEQ ID NO: 16.

The antibody of the present invention has a specific binding activity to human aggrecanase.

The "human aggrecanase" means that the amino acid sequence or nucleotide sequence of aggrecanase has an amino acid sequence or nucleotide sequence which is the same as or substantially the same as the amino acid sequence or nucleotide sequence of aggrecanase naturally expressed in human. The "substantially the same" means that the amino acid sequence or nucleotide sequence of interest has 70% or more (preferably 80% or more, more preferably 90% or more, further preferably 95% or more, most preferably 99% or more) identity with the amino acid sequence or nucleotide sequence of a particular aggrecanase naturally expressed in human, and has the function of the particular human aggrecanase. Biological species other than human, proteins other than aggrecanase, gene and fragments thereof are also interpreted in the same manner.

The "specific binding" of an antibody to antigen X means that the binding affinity of an antibody to antigen X in an antigen-antibody reaction is higher than the binding affinity to a non-specific antigen (e.g., bovine serum albumin (BSA)).

The antibody of the present invention has an activity to inhibit the enzymatic activity of human aggrecanase. The enzymatic activity of human aggrecanase specifically means an activity of human aggrecanase to cleave aggrecan (e.g., human or swine aggrecan). The activity of human aggrecanase to cleave aggrecan can be evaluated by incubating swine aggrecan and human aggrecanase at 37° C. for 16 hr, deglycosylating them with chondroitinase ABC and keratanase, and analyzing the obtained reaction product by immunoblotting using an anti-NITEGE$^{392}$ aggrecan neo-epitope antibody according to, for example, the methods described in Yatabe T, et.al. Ann Rheum Dis. 2009; 68:1051-8 and Hashimoto G, et al. J Biol Chem. 2004; 279:32483-91.

In a preferable embodiment, the antibody of the present invention has a specific binding activity to human ADAMTS4, and inhibits the aggrecanase activity of human ADAMTS4.

The antibody of this embodiment preferably also inhibits, in addition to the aggrecanase activity of human ADAMTS4, the aggrecanase activity of human ADAMTS5.

In the present specification, the "antibody" is used as one encompassing a full-length antibody and any antigen-binding fragment (i.e., "antigen-binding portion") thereof or a single chain thereof. The "antibody" refers to a glycoprotein containing at least two heavy chains (H) and two light chains (L), which are linked by a disulfide bond, or an antigen-binding portion thereof. Each heavy chain is constituted by a heavy chain variable region (to be abbreviated as $V_H$ herein) and a heavy chain constant region. The heavy chain constant region is constituted by 3 domains of $C_H1$, $C_H2$ and $C_H3$. Each light chain is constituted by a light chain variable region (to be abbreviated as $V_L$ herein) and a light chain constant region. The light chain constant region is constituted by a single domain $C_L$. $V_H$ and $V_L$ regions are further subdivided into regions with higher variability called complementarity determining regions (CDRs), which contain more highly conservative regions called framework regions (FRs) scattered therein. Each $V_H$ and $V_L$ is constituted by 3 CDRs and 4 FRs, which are aligned in the following order, i.e., FR1, CDR1, FR2, CDR2, FR3, CDR3, FR4 from the amino terminal to the carboxy terminal. The variable regions of said heavy chain and light chain contain binding domains that interact with an antigen. The constant region of an antibody can mediate the binding of immunoglobulin to host tissues or factors, including various cells (e.g., effector cells) of the immune system and the first component (C1q) of the conventional complement system.

In the present specification, the "antigen-binding portion" of an antibody is used to refer to one or more fragments of an antibody retaining an ability to specifically bind to an antigen (e.g., human ADAMTS4). It has been clarified that the antigen binding function of an antibody is performed by a fragment of a full-length antibody. Examples of the binding fragment included in the term "antigen binding portion" of an antibody include (i) Fab fragment, a monovalent fragment constituted by $V_L$, $V_H$, $C_L$ and $C_{H1}$ domains, (ii) F(ab')$_2$ fragment, a divalent fragment containing two Fab fragments linked by disulfide bond in the hinge region, (iii) Fab' fragment, an inherent Fab having a hinge region portion (see FUNDAMENTAL IMMUNOLOGY, Paul ed., 3. sup. rd ed. 1993), (iv) Fd fragment constituted by $V_H$ and $C_{H1}$ domains, (v) Fv fragment constituted by $V_L$ and $V_H$ domains in a single arm of an antibody, (vi) dAb fragment constituted by $V_H$ domain (Ward et al., (1989) Nature 341:544-546), (vii) isolated complementarity determining region (CDR) and (viii) nanobody which is a heavy chain variable region containing single variable domain and two constant regions. While $V_L$ and $V_H$, which are the two domains of Fv fragment, are encoded by different genes, they can be linked by a synthetic linker to produce a single protein chain from them by recombinant techniques, wherein, in this chain, $V_L$ and $V_H$ regions pair with each other to form a monovalent molecule (known as a single chain Fv (scFv); see, for example, Bird et al. (1988) Science 242: 423-426; and Huston et al., (1988) Proc. Natl. Acad. Sci. USA 85: 5879-5883). Such single chain antibody is also encompassed in the "antigen-binding portion" of an antibody. Such antibody fragments are obtained by those of ordinary skill in the art by known conventional techniques, and screened for usefulness in the same manner as with unmodified antibody.

The antibody of the present invention is preferably a monoclonal antibody. The "monoclonal antibody" refers to a preparation of an antibody molecule of a single molecule composition. The monoclonal antibody composition shows single binding-specificity and affinity for a particular epitope.

The antibody of the present invention is preferably a human antibody or a humanized antibody. The "human antibody" refers to an antibody having variable regions derived from a human germline immunoglobulin sequence in both the framework and CDR regions. Furthermore, when an antibody contains a constant region, the constant region also derives from a human germline immunoglobulin sequence. In the present specification, the "human antibody" also encompasses even an embodiment including an amino acid residue not encoded by a human germline immunoglobulin sequence (e.g., mutation introduced by random or site-directed mutagenesis in vitro or somatic mutation in vivo). In the present specification, moreover, the "humanized antibody" refers to an antibody wherein a CDR sequence derived from the germline of an animal species other than human, such as mouse, is fused on the human framework sequence.

In the present specification, the human antibody encompasses a "reconstituted human antibody". The reconstituted human antibody refers to a modified antibody wherein at least one CDR contained in the first human donor antibody is used in the second human acceptor antibody, instead of CDR of the second human acceptor antibody. Preferably, all 6 CDRs are substituted. More preferably, the whole antigen binding region (e.g., Fv, Fab or F(ab')2) of the first human donor antibody is used instead of the corresponding region in the second human acceptor antibody. More preferably, the Fab region of the first human donor antibody is operably linked to an appropriate constant region of the second human acceptor antibody to form a full-length antibody.

The reconstituted human antibody can be produced by conventional gene recombinant techniques disclosed in, for example, EP125023, WO96/02576, the above-mentioned document 15 and the like. To be specific, for example, a DNA sequence designed to link a desired CDR in a donor human antibody and a desired framework region (FR) in an acceptor human antibody is synthesized by PCR method using, as primers, several oligonucleotides produced to have a region overlapping with the terminal regions of both CDR and FR (see the method described in WO98/13388). The obtained DNA is linked to a DNA encoding a human antibody constant region or a human antibody constant region mutant, which is incorporated into a expression vector and the vector is introduced into a host to allow for production, whereby a reconstituted human antibody can be obtained (see EP125023, WO96/02576).

In the present specification, moreover, the human antibody encompasses an "artificial human antibody". The artificial human antibody can be produced by conventional gene recombinant techniques disclosed in, for example, the above-mentioned document 15 and the like.

The antibody of the present invention also includes a fusion protein wherein the aforementioned antibody and other peptide or protein are fused. The production method of a fusion protein includes linking a polynucleotide encoding the antibody of the present invention and a polynucleotide encoding other peptide or polypeptide to match the frame, introducing same into an expression vector, and allowing expression thereof in a host, and techniques known to those of ordinary skill in the art can be used. As other peptide to be fused with the antibody of the present invention, known peptides such as FLAG (Hopp, T. P. et al., BioTechnology (1988) 6, 1204-1210), 6xHis consisting of six His (histidine) residues, 10xHis, human c-myc fragment, VSV-GP fragment, p18HIV fragment, T7-tag, HSV-tag, E-tag, SV40T antigen fragment, lck tag, α-tubulin fragment, B-tag, Protein C fragment and the like can be used. Examples of other polypeptide to be fused with the antibody of the present invention include GST (glutathione-S-transferase), HA (influenza hemagglutinin), immunoglobulin constant region, β-galactosidase, MBP (maltose binding protein) and the like. A commercially available polynucleotide encoding such peptide or polypeptide is fused with a polynucleotide encoding the antibody of the present invention, and a fusion polynucleotide prepared thereby is expressed, whereby a fusion polypeptide can be prepared.

The antibody of the present invention may be a conjugate antibody bound with various molecules, for example, polymer substances such as polyethylene glycol (PEG), hyaluronic acid and the like, radioactive substance, fluorescent substance, luminescence substance, enzyme, toxin and the like. Such conjugate antibody can be obtained by chemically modifying the obtained antibody. The modification method of antibody has already been established in this field (e.g., U.S. Pat. Nos. 5,057,313, 5,156,840).

The antibody of the present invention is preferably isolated or purified. Being "isolated or purified" means that an operation to remove components other than the component of interest has been applied to the state of natural presence. The purity of the isolated or purified antibody of the present invention (ratio of the weight of the antibody of the present invention to the total protein weight) is generally 50% or more, preferably 70% or more, more preferably 90% or more, most preferably 95% or more (for example, substantially 100%).

In a particular embodiment, the antibody of the present invention specifically binds to human ADAMTS4 in an epitope containing the amino acid sequence depicted in SEQ ID NO: 9 (YCEGRRTRF), and inhibits the aggrecanase activity of human ADAMTS4.

The epitope containing the amino acid sequence depicted in SEQ ID NO: 9 includes, for example, an epitope consisting of a continuous partial sequence of the amino acid sequence depicted in SEQ ID NO: 15, which contains the amino acid sequence depicted in SEQ ID NO: 9, and preferably has an amino acid length of 20 or less, more preferably 12 or less. As the epitope containing the amino acid sequence depicted in SEQ ID NO: 9, specifically, an epitope consisting of the amino acid sequence depicted in SEQ ID NO: 9,
an epitope consisting of the amino acid sequence depicted in SEQ ID NO: 10 (GGKYCEGRRTRF),
an epitope consisting of the amino acid sequence depicted in SEQ ID NO: 11 (GKYCEGRRTRFR),
an epitope consisting of the amino acid sequence depicted in SEQ ID NO: 12 (KYCEGRRTRFRS), and
an epitope consisting of the amino acid sequence depicted in SEQ ID NO: 13 (YCEGRRTRFRSC)
can be mentioned.

The amino acid sequence depicted in SEQ ID NO: 9 is a partial amino acid sequence of human ADAMTS4, and does not show very high identity with the corresponding partial sequence of human ADAMTS5. Surprisingly, however, an antibody that specifically binds to human ADAMTS4 in an epitope containing the amino acid sequence depicted in SEQ ID NO: 9 can also inhibit the aggrecanase activity of human ADAMTS5 in addition to the aggrecanase activity of human ADAMTS4.

Specific examples of the antibody that specifically binds to human ADAMTS4 and inhibits the aggrecanase activity of human ADAMTS4 include the antibodies described in (1) or (2) below: (1) an antibody comprising a light chain variable region and a heavy chain variable region,
wherein the light chain variable region comprises CDR1 comprising the amino acid sequence depicted in SEQ ID NO: 1, CDR2 comprising the amino acid sequence depicted in SEQ ID NO: 2 and CDR3 comprising the amino acid sequence depicted in SEQ ID NO: 3, and
the heavy chain variable region comprises CDR1 comprising the amino acid sequence depicted in SEQ ID NO: 4, CDR2 comprising the amino acid sequence depicted in SEQ ID NO: 5 and CDR3 comprising the amino acid sequence depicted in SEQ ID NO: 6; and
(2) an antibody comprising a light chain variable region and a heavy chain variable region,
wherein the light chain variable region comprises CDR1 comprising the amino acid sequence depicted in SEQ ID NO: 1, CDR2 comprising the amino acid sequence depicted in SEQ ID NO: 2 and CDR3 comprising the amino acid sequence depicted in SEQ ID NO: 3, and
the heavy chain variable region comprises CDR1 comprising the amino acid sequence depicted in SEQ ID NO: 4, CDR2 comprising the amino acid sequence depicted in SEQ ID NO: 5 and CDR3 comprising the amino acid sequence depicted in SEQ ID NO: 6, except that 1 to 3 amino acids are substituted, deleted, inserted, and/or added in at least one amino acid sequence selected from the group consisting of SEQ ID NO: 1 to 3, and/or 1 to 3 amino acids are substituted, deleted, inserted, and/or added in at least one amino acid sequence selected from the group consisting of SEQ ID NO: 4 to 6.

In the embodiment of (2), 1-3 (preferably 1 or 2, more preferably 1) amino acids are preferably substituted, deleted, inserted, and/or added only in the amino acid sequence of CDR3 in the light chain variable region.

Examples of the method for substituting one or plural amino acid residues with other desired amino acid include site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Using these methods, desired amino acid in an antibody can be substituted by other amino acid of interest. Also, using the library technique such as framework shuffling (Mol Immunol. 2007 April; 44(11): 3049-60) and CDR repair (US2006/0122377) and the like, an amino acid in a framework or CDR can also be substituted by other appropriate amino acid.

In the antibody of the present invention, as a framework region (FR) of the antibody to be linked to a CDR, a framework which enables the CDR to form a good antigen binding site is selected. While FR to be used for the antibody of the present invention is not particularly limited and any FR can be used, FR of a human antibody is preferably used. As the FR of a human antibody, one having a natural sequence may be used, or one or plural amino acids in the framework region having a natural sequence may be substituted, deleted, added and/or inserted and the like as necessary, so that CDR will form an appropriate antigen binding site. For example, a mutant FR sequence having desired properties can be selected by measuring and evaluating the binding activity of an antibody having FR with substituted amino acid to an antigen (Sato, K. et al., Cancer Res. (1993)53, 851-856).

In the antibodies of (1) and (2), FR of Vk4 (Kabat database) of human antibody is preferably used for the light chain, and FR of VH1a (Kabat database) of human antibody is preferably used for the heavy chain.

The constant region used for the antibody of the present invention is not particularly limited, and any constant region may be used. Preferable examples of the constant region used for the antibody of the present invention include constant regions of human antibody (constant regions derived from IgG1, IgG2, IgG3, IgG4, IgA, IgM and the like). For example, Cγ1, Cγ2, Cγ3, Cγ4, Cμ, Cδ, Cα1, Cα2, Cε can be used in H chain, and Cκ, Cλ can be used in L chain.

In the antibodies of (1) and (2), the constant region of Cκ of human antibody is preferably used for the light chain, and the constant region of Cγ1 of human antibody is preferably used for the heavy chain.

Preferable antibody of the present invention includes the following:
(1') An antibody comprising a light chain variable region and a heavy chain variable region, wherein the light chain variable region comprises the amino acid sequence depicted in SEQ ID NO: 7 and the heavy chain variable region comprises the amino acid sequence depicted in SEQ ID NO: 8.

The antibody of the above-mentioned (1') corresponds to a preferable embodiment of the antibody of the above-mentioned (1).

The antibodies of the above-mentioned (1) and (2) preferably also inhibit aggrecanase activity of human ADAMTS5 in addition to the aggrecanase activity of human ADAMTS4.

In a particular embodiment, the antibodies of the above-mentioned (1) and (2) specifically bind to human ADAMTS4 in an epitope containing the amino acid sequence depicted in SEQ ID NO: 9 and inhibit aggrecanase activity of human ADAMTS4. Said antibodies can also inhibit aggrecanase activity of human ADAMTS5 in addition to the aggrecanase activity of human ADAMTS4.

The present invention provides a polynucleotide containing a nucleotide sequence encoding the above-mentioned antibody of the present invention. The polynucleotide may be a DNA or RNA, or a DNA/RNA chimera. The polynucleotide may be double stranded or single stranded. When the polynucleotide is double stranded, it may be a double stranded DNA, a double stranded RNA or a DNA:RNA hybrid.

The polynucleotide of the present invention encompasses a polynucleotide containing a nucleotide sequence encoding both the heavy chain variable region and the light chain variable region of the antibody of the present invention, and a combination of a polynucleotide containing a nucleotide sequence encoding the heavy chain variable region of the antibody of the present invention and a polynucleotide containing a nucleotide sequence encoding the light chain variable region of the antibody of the present invention.

The polynucleotide of the present invention can be easily produced based on the information of the amino acid sequence of the antibody of the present invention, known sequence information and sequence information described in the Sequence Listing in the present specification, and by utilizing known gene recombination techniques. For example, suitable primers are designed based on the sequence information, a DNA encoding the elements constituting the antibody of the present invention is amplified by the PCR reaction, DNA fragments are ligated by appropriate enzymes such as ligase and the like, whereby the polynucleotide of the present invention can be produced. Alternatively, a polynucleotide encoding each element may be synthesized by a polynucleotide synthesizer, based on the information of the amino acid sequence of the antibody of the present invention.

The obtained polynucleotide encoding the antibody of the present invention may be, depending on the object, directly used, or used after digestion with a restriction enzyme when desired, or addition of a linker. The polynucleotide may have ATG as a translation initiation codon on the 5' terminal side, and may have TAA, TGA or TAG as a translation stop codon on the 3' terminal side. These translation initiation codon and translation stop codon can be added using a suitable synthesized DNA adapter.

The polynucleotide of the present invention is preferably isolated or purified. The isolated or purified polynucleotide of the present invention has a purity (ratio of the weight of the polynucleotide of the present invention to the total polynucleotide weight) of generally 50% or more, preferably 70% or more, more preferably 90% or more, most preferably 95% or more (for example, substantially 100%).

The present invention provides a vector comprising the above-mentioned polynucleotide of the present invention. The vector of the present invention encompasses a vector comprising a polynucleotide comprising a nucleotide sequence encoding both the heavy chain variable region and the light chain variable region of the antibody of the present invention, and a combination of a vector comprising a polynucleotide comprising a nucleotide sequence encoding the heavy chain variable region of the antibody of the present invention and a vector comprising a polynucleotide comprising a nucleotide sequence encoding the light chain variable region of the antibody of the present invention. The vector is preferably isolated or purified. Examples of the vector include expression vector, cloning vector and the like, which can be selected according to the object. Preferably, the vector is an expression vector. The expression vector can express the antibody of the present invention. The expression vector can be produced by operably linking the polynucleotide of the present invention to the downstream of a promoter in a suitable expression vector. The kind of the vector includes, for example, plasmid vector, virus vector and the like, which can be appropriately selected according to the host to be used.

As the host, the genus *Escherichia* (*Escherichia coli* etc.), the genus *Bacillus* (*Bacillus subtilis* etc.), yeast (*Saccharomyces cerevisiae* etc.), insect cell (established cell line derived from larva of *Mamestra brassicae* (*Spodoptera frugiperda* cell; Sfcell) etc.), insect (larva of *Bombyx mori* etc.), mammalian cells (rat nerve cell, monkey cell (COS-7 etc.), Chinese hamster cell (CHO cell etc.) etc.) and the like are used.

Examples of the mammal include, but are not limited to, experiment animals such as rodents such as mouse, rat, hamster and guinea pig and the like, rabbit and the like, domestic animals such as swine, bovine, goat, horse, sheep, mink and the like, companion animals such as dog, cat and the like, primates such as human, monkey, *Macaca fascicularis, Macaca mulatta*, marmoset, orangutan, chimpanzee and the like, and the like.

Examples of the plasmid vector include plasmid vectors derived from *Escherichia coli* (e.g., pBR322, pBR325, pUC12, pUC13), plasmid vectors derived from *Bacillus subtilis* (e.g., pUB110, pTP5, pC194), plasmid vectors derived from yeast (e.g., pSH19, pSH15) and the like, which can be appropriately selected according to the kind of the host to be used and the object of use.

The kind of the virus vector can be appropriately selected according to the kind of the host to be used and object of use. For example, when an insect cell is used as a host, baculovirus vector and the like can be used. When a mammalian cell is used as a host, retrovirus vectors such as moloney murine leukemia virus vector, lentivirus vector, sindbis virus vector and the like, adenovirus vector, herpes virus vector, adeno-associated virus vector, parvovirus vector, vaccinia virus vector, sendai virus vector and the like can be used.

The promoter can be selected according to the kind of the host to be used, and one capable of initiating transcription in the host can be selected. For example, when the host is the genus *Escherichia*, trp promoter, lac promoter, T7 promoter and the like are preferable. When the host is the genus *Bacillus*, SPOT promoter, SPO2 promoter, penP promoter and the like are preferable. When the host is yeast, PHO5 promoter, PGK promoter and the like are preferable. When the host is an insect cell, polyhedrin promoter, P10 promoter and the like are preferable. When the host is a mammalian cell, subgenomic (26S) promoter, CMV promoter, SRα promoter and the like are preferable.

The vector of the present invention may contain a signal sequence for antibody secretion. As the signal sequence for antibody secretion when it is produced in the periplasm of *Escherichia coli*, pelB signal sequence (Lei, S. P. et al J. Bacteriol. (1987) 169, 4379) may be used.

When desired, the vector of the present invention may contain enhancer, splicing signal, polyA addition signal, selection marker, SV40 replication origin (hereinafter sometimes to be abbreviated as SV40ori) and the like each in an operable manner. Examples of the selection marker include dihydrofolate reductase (hereinafter sometimes to be abbreviated as dhfr) gene [methotrexate (MTX) resistance], ampicillin resistance gene (sometimes to be abbreviated as Amp$^r$), neomycin resistance gene (sometimes to be abbreviated as Neo$^r$, G418 resistance) and the like.

By introducing the above-mentioned vector of the present invention into the above-mentioned host by gene transfer methods known per se (e.g., lipofection method, calcium phosphate method, microinjection method, proplast fusion method, electroporation method, DEAE dextran method, gene transfer method by Gene Gun etc.), a transformant with the vector introduced thereinto (transformant of the present invention) can be produced. When an expression vector is used as the vector to be introduced, the transformant can express the antibody of the present invention. The transformant of the present invention is useful for the production of the antibody of the present invention and the like.

The antibody of the present invention can be produced by culturing the transformant of the present invention by a method known per se according to the kind of the host, and isolating the antibody of the present invention from the culture. When the host is the genus *Escherichia*, the transformant is cultured in an appropriate medium such as LB medium, M9 medium and the like at generally about 15-43° C. for about 3-24 hr. When the host is the genus *Bacillus*, the transformant is cultured in an appropriate medium generally at about 30-40° C. for about 6-24 hr. When the host is yeast, the transformant is cultured in an appropriate medium such as Burkholder's medium and the like generally at about 20° C.-35° C. for about 24-72 hr. When the host is an insect cell or insect, the transformant is cultured in an appropriate medium such as Grace's Insect medium added with about 10% of bovine serum and the like generally at about 27° C. for about 3-5 days. When the host is an animal cell, the transformant is cultured in an appropriate medium such as MEM medium added with about 10% of bovine serum and the like generally at about 30° C.-40° C. for about 15-60 hr. In any culture, aeration and stirring may be performed as necessary.

As for the production method of antibody by genetic engineering, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137 and the like can be referred to.

The separation and purification of the antibody of the present invention from a culture is not limited in any manner, and the separation and purification methods generally used for purification of antibody can be employed. For example, antibody can be separated and purified by appropriately selecting and combining chromatography column, filter, ultrafiltration, salting out, solvent precipitation, solvent extraction, distillation, immunoprecipitation, SDS-polyacrylamide gel electrophoresis, isoelectric focusing, dialysis, recrystallization and the like.

Examples of the chromatography include affinity-chromatography, ion exchange chromatography, hydrophobic chromatography, gelfiltration, reversed-phase chromatography, adsorption chromatography and the like (Strategies for Protein Purification and Characterization: A Laboratory Course Manual. Ed Daniel R. Marshak et al., Cold Spring Harbor Laboratory Press, 1996). These chromatographys can be performed by using liquid phase chromatography, for example, liquid phase chromatography such as HPLC, FPLC and the like. Examples of the column to be used for affinity chromatography include protein A column and protein G column. For example, as a column using protein A, Hyper D, POROS, Sepharose FF (manufactured by GE Amersham Biosciences) and the like can be mentioned. The present invention also encompasses an antibody highly purified by these purification methods.

In addition, the present invention provides a pharmaceutical composition containing the above-mentioned antibody of the present invention as an active ingredient. Aggrecanases (particularly, ADAMTS4 and 5) degrade aggrecan and contribute to the cartilage destruction in arthritis such as osteoarthritis, rheumatoid arthritis and the like. Therefore, administration of the antibody of the present invention inhibits aggrecanase activity, suppresses aggrecan degradation, suppresses cartilage destruction and, as a result, can prevent or treat progression of arthritis. Accordingly, the antibody of the present invention and the pharmaceutical composition of the present invention are useful as prophylactic or therapeutic agents for the progression of arthritis and the like. Particularly, the antibody of the present invention in the embodiment wherein the antibody inhibits not only the aggrecanase activity of human ADAMTS4 but also the aggrecanase activity of human ADAMTS5 can simultaneously inhibit plural kinds of aggrecanases. Therefore, a superior cartilage denaturation or destruction suppressive effect, and a superior prophylactic or therapeutic effect on arthritis can be expected. The kind of arthritis is not particularly limited as long as it accompanies cartilage destruction or denaturation due to aggrecan degradation by aggrecanase (particularly, ADAMTS4 and 5), and the antibody of the present invention provides a prophylactic or therapeutic effect. Examples thereof include, but are not limited to, articular cartilage denaturation or destruction due to aggrecan degradation in, for example, osteoarthritis, rheumatoid arthritis, ankylosing arthritis, psoriatic arthritis and the like, denaturation and destruction of intervertebral disc in disc hernia and the like.

Furthermore, since the involvement of ADAMTS4 and 5 in the infiltration of brain tumor cells due to the Brevican degradation in brain tumor (glioblastoma multiforme), vascular destruction due to Versican degradation in intractable vasculitis, skin tissue destruction, excess repair action and the like due to Versican degradation and the product thereof in skin chronic ulcer, keloid and the like has been pointed out, the antibody of the present invention and the pharmaceutical composition of the present invention are also useful as prophylactic or therapeutic agents for the progression of these diseases and the like.

When the antibody of the present invention is "contained as an active ingredient", it means that the antibody of the present invention is contained as at least one of the active ingredients, and does not limit the content thereof. The pharmaceutical composition of the present invention may contain other active ingredient(s) together with the antibody of the present invention.

The antibody of the present invention can be formulated according to a conventional method (e.g., Remington's Pharmaceutical Science, latest edition, Mark Publishing Company, Easton, U.S.A). Where necessary, moreover, it may contain a pharmaceutically acceptable carrier and/or additive. For example, it can contain surfactant (PEG, Tween etc.), excipient, antioxidant (ascorbic acid etc.), colorant, flavor, preservative, stabilizer, buffering agent (phosphate, citrate, other organic acid etc.), chelating agent (EDTA etc.), suspending agent, isotonizing agent, binder, disintegrant, lubricant, glidant, corrigent and the like. Not being limited to these, the pharmaceutical composition of the present invention may contain other conventional carriers as appropriate. Specific examples include light anhydrous silicic acid, lactose, crystalline cellulose, mannitol, starch, carmellose calcium, carmellose sodium, hydroxypropylcellulose, hydroxypropylmethylcellulose, polyvinyl acetaldiethylaminoacetate, polyvinylpyrrolidone, gelatin, medium-chain fatty acid triglyceride, polyoxyethylene hydrogenated castor oil 60, sucrose, carboxymethylcellulose, cornstarch, inorganic salts and the like. It may also contain other low-molecular-weight polypeptide, serum albumin, gelatin and protein such as immunoglobulin and the like, as well as amino acid. When an aqueous solution for injection is formulated, the antibody of the present invention is dissolved in, for example, isotonic solution containing saline, glucose or other auxiliary agent. Examples of the auxiliary agent include D-sorbitol, D-mannose, D-mannitol, and sodium chloride, and may be used in combination with suitable solubilizing agents, for example, alcohol (ethanol etc.), polyalcohol (propylene glycol, PEG etc.), non-ionic surfactant (polysorbate80, HCO-50) and the like.

Where necessary, polypeptide may also be included in a microcapsule (microcapsules made of hydroxymethylcellulose, gelatin, poly[methylmethacrylate] and the like), or formulated as a colloid drug delivery system (liposome, albumin microsphere, microemulsion, nanoparticles and nanocapsule etc.) (see Remington's Pharmaceutical Science 16th edition &, Oslo Ed. (1980) etc.). Furthermore, a method of formulating a drug as a sustained-release medicament is also known, and applicable to polypeptide (Langer et al., J. Biomed. Mater. Res. (1981)15: 167-277; Langer, Chem. Tech. (1982)12: 98-105; U.S. Pat. No. 3,773,919; EP-A-58, 481; Sidman et al., Biopolymers (1983) 22: 547-56; EP No. 133,988). Furthermore, it is also possible to increase the liquid amount to be subcutaneously administered by adding or blending hyaluronidase to or with the present agent (e.g., WO 2004/078140 etc.).

The content of the antibody of the present invention in a pharmaceutical composition is, for example, about 0.01-100 wt %, preferably 0.1-99.9%, of the whole pharmaceutical composition.

While the pharmaceutical composition of the present invention can be administered both orally and parenterally, it is preferably administered parenterally. Specifically, it is administered to patients by injection or transdermal administration. As an example of the dosage form of injection, it can be administered systemically or topically by intravenously injection, intramuscular injection, subcutaneous injection and the like. It may also be administered to the treatment site or in the vicinity thereof by topical injection, particularly intramuscular injection. Examples of the dosage form of transdermal administration include ointment, gel, cream, plaster, patch and the like, which can be administered systemically or topically. In addition, the administration method can be appropriately selected according to the age and symptom of the patients. The dose can be selected from, for example, the range of 0.5 mg-10 mg/kg body weight as the antibody of the present invention. However, the pharmaceutical composition of the present invention is not limited by these doses.

All references cited in the present specification, including publication, patent document and the like, are hereby incorporated individually and specifically by reference, to the extent that the entireties thereof have been specifically disclosed herein.

EXAMPLES

The present invention is explained in more detail in the following by referring to Examples, which are not to be construed as limitative. Various gene manipulations in the Examples followed the method described in Molecular cloning third. ed. (Cold Spring Harbor Lab. Press, 2001).
Materials and Methods
Phage Display Library Panning and Fab Generation.

Production of monoclonal Fab antibodies specific to ADAMTS4 and ADAMTS5 were generated using the Human Combinatorial Antibody Library (HuCAL; MorphoSys AG, Martinried, Germany). Recombinant ADAMTS4 and ADAMTS5 (R&D Systems Inc., Minneapolis, Minn.) were biotinylated and incubated with HuCAL. Bound Fab expressing phages were enriched in three consecutive panning rounds. The pool of Fab genes was isolated from phagemids and inserted into *Escherichia coli* expression vectors that lead to functional periplasmic expression of Fab equipped with Strep-tag II. After transformation, individual colonies were picked up and grown in microtiter plates. After induction of antibody expression by incubation with isopropyl-β-thiogalactopyranoside overnight, the cells were enzymatically lysed and the crude extracts were tested by enzyme-linked immunosorbent assay (ELISA). The DNA sequences of the antibody VH CDR regions were determined for clones that gave strong signals on the antigens in the ELISA. Colonies containing Fabs were chosen for subsequent purification, and some of the Fabs were reformatted into whole human IgG1 for further experiments.

Recombinant Human ADAMTS4 and ADAMTS5.

Expression vectors containing cDNA fragments encoding the residues Phe$^{213}$-Cys$^{685}$ of human ADAMTS4, which correspond to the metalloproteinase, disintegrin, thrombospondin and cysteine-rich domains of ADAMTS4, with the Strep-tag II at the C-terminal were transfected to HEK293T cells using Lipofectamine (Life Technologies, Rockville, Md.). The culture media were harvested at 2 days after the transfection, and recombinant human ADAMTS4 was purified by using the Strep-Tactin Sepharose according to manufacturer's instructions (IBA Biotechnica, Hanover, Germany). Recombinant ADAMTS5 protein containing the metalloproteinase, disintegrin and thrombospondin domains (residues of Ser$^{262}$-Pro$^{622}$ of ADAMTS5) was purchased from R&D Systems Inc.

Immunoblotting of Human Anti-ADAMTS1 Antibodies.

Recombinant proteins of human ADAMTS1 (R&D Systems), ADAMTS4, ADAMTS5 (R&D Systems), ADAMTS15 (R&D Systems), ADAM10 (R&D Systems), ADAM12 (Mochida Pharmaceutical Co., Ltd., Tokyo, Japan), ADAM17 (R&D Systems) and MMP-13 (Millipore, Billerica, Mass.) and purified human MMP-1, MMP-2, MMP-3 and MMP-9 (Daiichi Fine Chemical, Co., Ltd., Toyama, Japan) were subjected to sodium dodecyl sulfate-polyacrylamide gel electrophoresis (SDS-PAGE) under reducing conditions, and the samples resolved on the gels were transferred onto polyvinylidene difluoride (PVDF) membranes. The membranes were incubated with candidate Fabs against ADAMTS species (5 µg/ml; clones 237-1, 237-5, 237-21, 237-43 and 237-53) at 4° C. for 16 h. After washing with phosphate buffered saline containing 0.1% Tween 20, the membranes were reacted with horseradish peroxidase-conjugated secondary antibody against human IgG (Invitrogen, Carlsbad, Calif.) for 1 h at room temperature. A chemiluminescence reagent (Pierce ECL western blotting substrate; Thermo Fisher Scientific, Waltham, Mass.) was used to make the labeled protein bands visible. All the samples were also examined on silver-stained gels, which were prepared by silver stain kit (Cosmo Bio Co., Ltd, Carlsbad, Calif.).

Inhibition of Aggrecanase Activity of ADAMTS4 and 5 with Human Anti-ADAMTS Antibody (Clone 237-53).

Recombinant ADAMTS4 (180 ng), and ADAMTS5 (180 ng) were incubated for 30 min at 37° C. with human anti-ADAMTS antibody (IgG1; clone 237-53) in molar ratios of 1:0.2-5 (enzyme:antibody) or human control normal IgG1 (R&D Systems), and then reacted with porcine aggrecan (100 µg) for 16 h at 37° C. After deglycosylation of aggrecan with chondroitinase ABC and keratanase (Seikagaku Corporation, Tokyo, Japan), aggrecanase activity was monitored by immunoblotting using the anti-NITEGE$^{392}$ aggrecan neoepitope antibody (1.2 µg/ml) (Hashimoto G, et al. J Biol Chem. 2004; 279:32483-91). Density of the protein band was evaluated by densitometry using Image J analysis software (National Institute of Health, Bethesda, Md.).

Domain Mapping of Anti-ADAMTS Antibody (clone 237-53).

Recombinant FLAG and dihydrofolic acid reductase (DHFR)-tagged proteins of each domain of ADAMTS4 and the thrombospondin domain with NH$_2$— or COOH-terminal deletion were synthesized using cell-free translation system (PUREfrex) (Gene Frontier Corporation, Chiba, Japan). These samples were subjected to SDS-PAGE and then immunoblotted with anti-FLAG antibody (Sigma-Aldrich, St Louis, Mo.; 2 µg/ml) or human anti-ADAMTS antibody (clone 237-53; 2 µg/ml).

Surface Plasma Resonance Interaction (BIAcore) Analysis

Recombinant ADAMTS species were covalently immobilized via amine coupling on CM5 sensor chip flow chambers (GE Healthcare Life Sciences, Buckinghamshire, UK). IgG1 of clone 237-53 was injected to the chambers using BIAcore 3000 (GE Healthcare Life Sciences). The $K_D$ (the affinity) was calculated from the determined $K_a$ and $K_d$ values.

Inhibition of Aggrecanase Activity in Cultured Chondrocytes with Anti-ADAMTS Antibody (Clone 237-53).

Chondrocytes isolated by enzymatic dissociation from human osteoarthritic cartilage were cultured in Dulbecco's modified Eagle medium/Ham's F-12 medium (Sigma-Aldrich) supplemented with 10% fetal bovine serum and 25 µg/ml of ascorbic acid, and treated with or without interleukin-1α (IL-1α (1 ng/ml; Dainippon Sumitomo Pharmaceutical Company Ltd., Okada, Japan) for 24 h after serum-starvation by culturing in the medium containing 0.2% lactalbumin hydrolysate. They were treated with ADAMTS antibody (5 µg/ml, clone 237-53) or human control IgG (5 µg/ml; Invitrogen, Carlsbad, Calif.) for 1 h, and then incubated in the presence of aggrecan (100 µg) for 16 h. The concentrated media were subjected to SDS-PAGE after deglycosylation and transferred onto PVDF membranes. Aggrecanase activity was evaluated by immunoblotting with anti-NITEGE$^{392}$ neoepitope antibody (1.2 µg/ml). Informed consent was obtained from the patients with osteoarthritis for the experimental use of the surgical samples according to the hospital ethics guidelines.

To examine the mRNA expression of ADAMTS4 and 5, total RNA was prepared from the chondrocytes treated with or without IL-1α (1 ng/ml) and human anti-ADAMTS antibody (clone 237-53) for 18 h, and reversed-transcribed to cDNAs using SuperScript II reverse transcriptase (Life Technologies, Rockville, Md.). The cDNAs were amplified by PCR with primers specific to ADAMTS4 and 5 and housekeeping gene glyceraldehyde-3-phosphate dehydrogenase (GAPDH) as described previously (Naito S, et. al. Pathol Int. 2007; 57:703-11).

Results

Screening of Human Antibodies Against ADAMTS4 and ADAMTS5

By screening human antibody library (HuCAL) using the phage display method, a total of 5 clones (237-1, 237-5, 237-21, 237-43 and 237-53) that were reactive with both ADAMTS4 and ADAMTS5 were obtained by ELISA. Immunoblotting analysis indicated that all the clones recognize recombinant ADAMTS4 and ADAMTS5, although the reactivity to ADAMTS5 was different among the clones (FIG. 1A). To examine whether the candidate clones inhibit aggrecanase activity of ADAMTS4, Fab species of the clones were incubated with ADAMTS4 in a molar ratio of 1:1, and then the activity was monitored by immunoblotting using the neo-epitope (NITEGE$^{392}$)-specific antibody. As shown in FIG. 1B, clone 237-53 inhibited the aggrecanase activity among the five candidate clones.

Immunoreactivity of Clone 237-53 with ADAMTS4 and ADAMTS5

Figure 2:
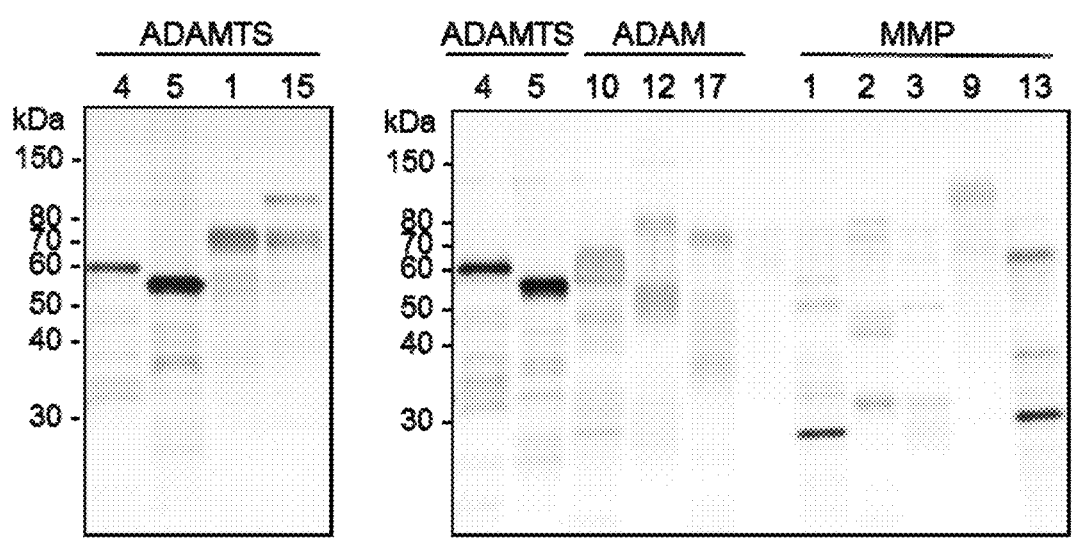
FIG. 2. Immunoreactivity of anti-ADAMTS antibody (clone 237-53) with ADAMTS, ADAM and MMP species. (A) Silver-stained gels of ADAMTS4, 5 and 1, ADAM10, 12 and 17, and MMP1, 2, 3, 9 and 13. The samples (100 ng/lane) were subjected to SDS-PAGE, and the gels were stained with silver stain kit. (B) Immunoreactivity of the antibody (clone 237-53) with the ADAMTS, ADAM and MMP species. The samples transferred on PVDF membranes were immunoblotted with anti-ADAMTS antibody clone 237-53. Note that the antibody reacts with ADAMTS4 and ADAMTS5, but not with other ADAMTS, ADAM and MMP species.
Figure 2:
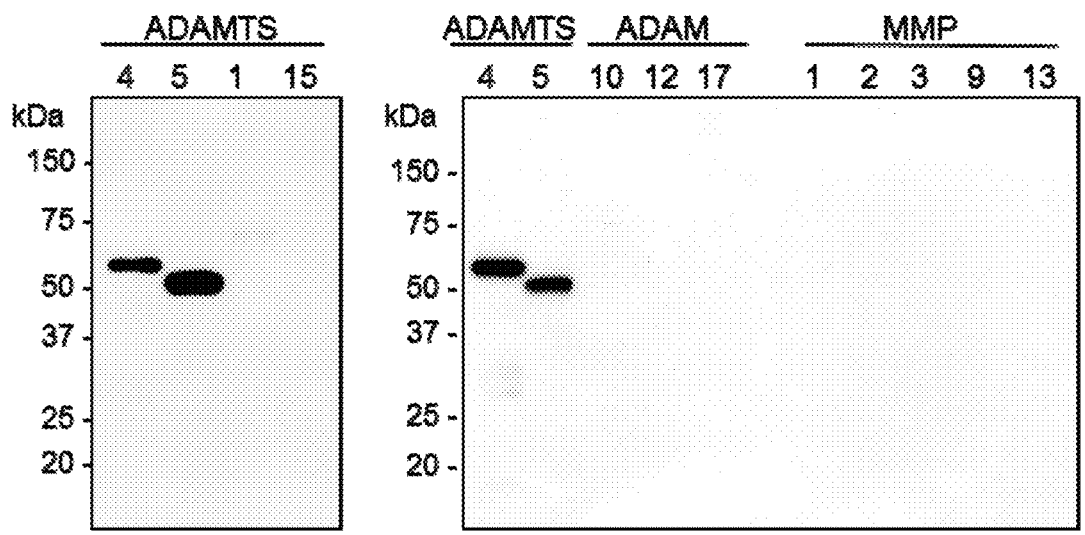

Since clone 237-53 showed inhibitory activity to ADAMTS4, this antibody was focused. When cross-reactivity of the antibody to ADAMTS, ADAM and MMP species was examined by immunoblotting, clone 237-53 reacted with ADAMTS4 and ADAMTS5. However, no immunoreactivity was obtained with ADAMTS1, ADAMTS15, ADAM10, ADAM12, ADAM17, MMP-1, MMP-2, MMP-3, MMP-9 or MMP-13 (FIG. 2). The data suggest that clone 237-53 reacts with some region commonly present in ADAMTS4 and ADAMTS5.

Determination of the Epitope of ADAMTS4 Recognized by Clone 237-53

Figure 3:
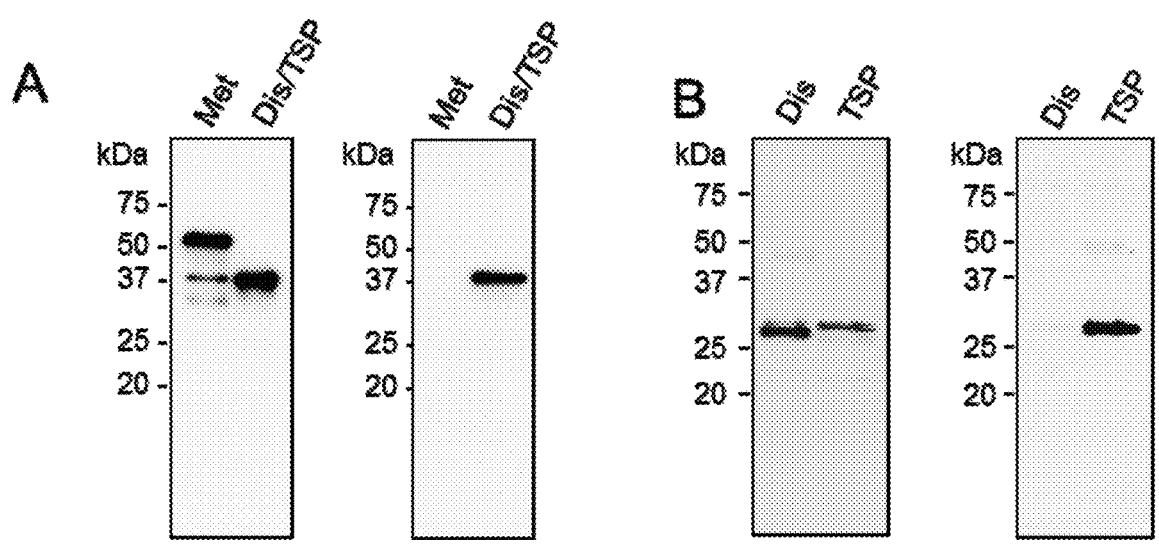
FIG. 3. Domain mapping analysis of anti-ADAMTS antibody (clone 237-53). (A and B) Immunoreactivity of the antibody with each domain of ADAMTS4. Recombinant FLAG/DHFR-tagged proteins corresponding to the metalloproteinase (Met) domain, disintegrin and thrombospondin domains (Dis/TSP), disintegrin (Dis) domain or thrombospondin (TSP) domain of ADAMTS4 were prepared by PUREfrex. These proteins were immunoblotted with anti-FLAG antibody (positive controls; left) or the antibody clone 237-53 (right).

To determine the immunoreactive domain of ADAMTS4 by the antibody clone 237-53, we first examined reactivity to the recombinant proteins of metalloproteinase domain alone or disintegrin and thrombospondin domains of ADAMTS4 generated by the PUREfrex. As shown in FIG. 3A, the antibody recognized only the protein of the disintegrin and thrombospondin domains. Thus, we further examined the immunoreactivity with disintegrin or thrombospondin domain, and found that the antibody recognizes only the thrombospondin domain (FIG. 3B), indicating that the thrombospondin domain of ADAMTS4 contains the epitope for the antibody.

To identify the epitope in more detail, a peptide array with immobilized partial peptides of human ADAMTS4 was used for epitope mapping of the antibody clone 237-53. To be specific, as shown in the following Table, a peptide array consisting of peptides having the residue number of 12 amino acid residues and an offset of 3 amino acid residues was produced relative to a sequence covering the thrombospondin domain of human ADAMTS4. HRP-labeled antibody clone 237-53 was reacted with the peptide array.

TABLE 1

| 1 | AGGWGPWGPWGD | (SEQ ID NO: 18) |
| 2 | GGWGPWGPWGDC | (SEQ ID NO: 19) |
| 3 | GWGPWGPWGDCS | (SEQ ID NO: 20) |
| 4 | WGPWGPWGDCSR | (SEQ ID NO: 21) |
| 5 | GPWGPWGDCSRT | (SEQ ID NO: 22) |
| 6 | PWGPWGDCSRTC | (SEQ ID NO: 23) |
| 7 | WGPWGDCSRTCG | (SEQ ID NO: 24) |
| 8 | GPWGDCSRTCGG | (SEQ ID NO: 25) |
| 9 | PWGDCSRTCGGG | (SEQ ID NO: 26) |
| 10 | WGDCSRTCGGGV | (SEQ ID NO: 27) |
| 11 | GDCSRTCGGGVQ | (SEQ ID NO: 28) |
| 12 | DCSRTCGGGVQF | (SEQ ID NO: 29) |
| 13 | CSRTCGGGVQFS | (SEQ ID NO: 30) |
| 14 | SRTCGGGVQFSS | (SEQ ID NO: 31) |
| 15 | RTCGGGVQFSSR | (SEQ ID NO: 32) |
| 16 | TCGGGVQFSSRD | (SEQ ID NO: 33) |
| 17 | CGGGVQFSSRDC | (SEQ ID NO: 34) |
| 18 | GGGVQFSSRDCT | (SEQ ID NO: 35) |
| 19 | GGVQFSSRDCTR | (SEQ ID NO: 36) |
| 20 | GVQFSSRDCTRP | (SEQ ID NO: 37) |
| 21 | VQFSSRDCTRPV | (SEQ ID NO: 38) |
| 22 | QFSSRDCTRPVP | (SEQ ID NO: 39) |
| 23 | FSSRDCTRPVPR | (SEQ ID NO: 40) |
| 24 | SSRDCTRPVPRN | (SEQ ID NO: 41) |

TABLE 1-continued

| 25 | SRDCTRPVPRNG | (SEQ ID NO: 42) |
| 26 | RDCTRPVPRNGG | (SEQ ID NO: 43) |
| 27 | DCTRPVPRNGGK | (SEQ ID NO: 44) |
| 28 | CTRPVPRNGGKY | (SEQ ID NO: 45) |
| 29 | TRPVPRNGGKYC | (SEQ ID NO: 46) |
| 30 | RPVPRNGGKYCE | (SEQ ID NO: 47) |
| 31 | PVPRNGGKYCEG | (SEQ ID NO: 48) |
| 32 | VPRNGGKYCEGR | (SEQ ID NO: 49) |
| 33 | PRNGGKYCEGRR | (SEQ ID NO: 50) |
| 34 | RNGGKYCEGRRT | (SEQ ID NO: 51) |
| 35 | NGGKYCEGRRTR | (SEQ ID NO: 52) |
| 36 | GGKYCEGRRTRF | (SEQ ID NO: 10) |
| 37 | GKYCEGRRTRFR | (SEQ ID NO: 11) |
| 38 | KYCEGRRTRFRS | (SEQ ID NO: 12) |
| 39 | YCEGRRTRFRSC | (SEQ ID NO: 13) |
| 40 | CEGRRTRFRSCN | (SEQ ID NO: 53) |
| 41 | EGRRTRFRSCNT | (SEQ ID NO: 54) |
| 42 | GRRTRFRSCNTE | (SEQ ID NO: 55) |
| 43 | RRTRFRSCNTED | (SEQ ID NO: 56) |
| 44 | RTRFRSCNTEDC | (SEQ ID NO: 57) |
| 45 | TRFRSCNTEDCP | (SEQ ID NO: 58) |

As a result, 237-53 specifically bound to the above-mentioned peptides #36-#39. The results suggest that the epitope of 237-53 contains the amino acid sequence depicted in SEQ ID NO: 9 (YCEGRRTRF) which is common to peptides #36-#39.

*Escherichia coli* of the obtained clone 237-53 was cultured, and plasmid was recovered (QIAprep Spin MiniPrep kit: manufactured by QIAGEN) and used for the DNA sequence analysis. Table 2 shows the amino acid sequences of CDRs (complementarity determining regions) of 237-53 H chain and L chain.

TABLE 2

| | light chain | | |
|---|---|---|---|
| | LCDR1 | LCDR2 | LCDR3 |
| 237-53 | RSSQSILYSSNNNYLA (SEQ ID NO: 1) | HTASARES (SEQ ID NO: 2) | QQYYSVSI (SEQ ID NO: 3) |
| | heavy chain | | |
| | HCDR1 | HCDR2 | HCDR3 |
| 237-53 | GTFSSFAIS (SEQ ID NO: 4) | GIFPIFGQANYAQKPQG (SEQ ID NO: 5) | FSDWWEWQMDY (SEQ ID NO: 6) |

The full-length amino acid sequences of the variable regions of H chain and L chain of 237-53 were as follows.

L chain VLk4
(SEQ ID NO: 7)
DIVMTQSPDSLAVSLGERATINCRSSQSILYSSNNNYLAWYQQKPGQPPK

LLIHTASARESGVPDRFSGSGSGTDFTLTISSLQAEDVAVYYCQQYYSVS

ITFGQGTKVEIKRT

H chain VH1a
(SEQ ID NO: 8)
QVQLVQSGAEVKKPGSSVKVSCKASGGTFSSFAISWVRQAPGQGLEWMGG

IFPIFGQANYAQKFQGRVTITADESTSTAYMELSSLRSEDTAVYYCARFS

DWWEWQMDYWGQGTLVTVSS

Inhibition of Aggrecanase Activity of ADAMTS4 and ADAMTS5 by the Antibody Clone 237-53

Figure 4:
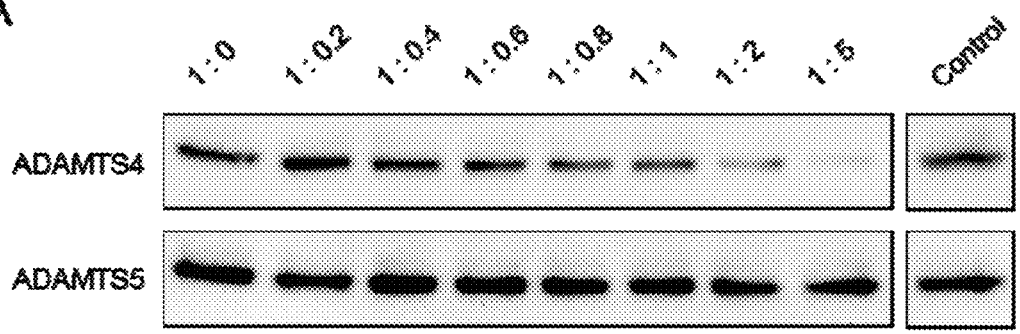
FIG. 4. Inhibition of aggrecanase activity of ADAMTS4 and ADAMTS5 by anti-ADAMTS antibody (clone 237-53), and effect of the antibody on the expression of the ADAMTS species and aggrecanase activity in IL-1α-stimulated chondrocytes. (A) Inhibition of aggrecanase activity of ADAMTS4 and ADAMTS5 by anti-ADAMTS antibody (clone 237-53). Recombinant ADAMTS proteins were reacted with anti-ADAMTS antibody in molar ratios of 1:0.2-5 (enzyme:antibody) or control normal IgG (Control; 1:5 molar ratio), and then incubated with aggrecan. The aggrecan digestion was monitored by immunoblotting with anti-aggrecan neoepitope antibody (upper). Inhibition was evaluated by densitometric analysis of the immunoblots (lower). (B) Effect of the antibody (clone 237-53) on the mRNA expression of ADAMTS4 and ADAMTS5 and aggrecanase activity in the IL-1α-stimulated chondrocytes. Osteoarthritic chondrocytes were cultured in the presence and absence of IL-1α and anti-ADAMTS antibody or control normal IgG (Control). Then, the mRNA expression of these ADAMTS species (left) and aggrecanase activity in the conditioned media (right) were examined by RT-PCR and immunoblotting with anti-aggrecan neoepitope antibody, respectively. GAPDH, a control for loaded samples.
Figure 4:
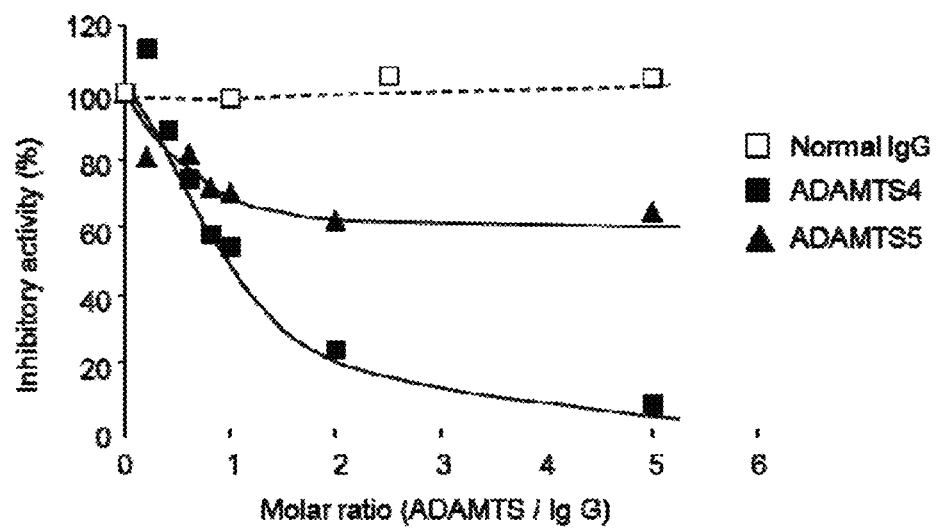
Figure 4:
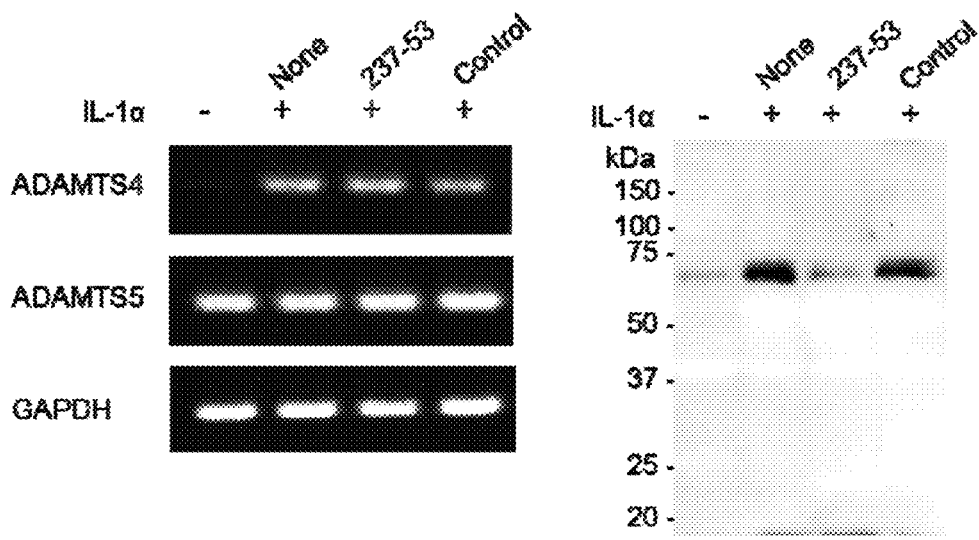

Aggrecanase activity of ADAMTS4 and ADAMTS5 was assayed by immunoblotting demonstration of the 65-kDa aggrecan fragments with the COOH-terminal sequence of NITEGE[392] using the aggrecan neoepitope-specific antibody. As shown in FIG. 4A, the antibody clone 237-53 blocked the activity of ADAMTS4 to less than 20% of the original activity, while the ADAMTS5 activity was slightly inhibited to approximately 70% of the original activity. No inhibition was observed with normal control IgG (FIG. 4A). Kinetic analysis using BIAcore demonstrated high affinity binding of this antibody to ADAMTS species, showing $K_D$ values of $1.17 \times 10^{-8}$ M and $1.46 \times 10^{-8}$ M for ADAMTS4 and ADAMTS5, respectively.

Cultured chondrocytes from osteoarthritic cartilage expressed ADAMTS5, but not ADAMTS4 (FIG. 4B, left). When the chondrocytes were treated with IL-1α, ADAMTS4 was induced, but the expression of ADAMTS5 was unchanged (FIG. 4B, left). Aggrecanase activity of the untreated chondrocytes was minimal, but it was increased after stimulation with IL-1α (FIG. 4B, right). When IL-1α-stimulated chondrocytes were treated with the antibody clone 237-53, the aggrecanase activity was substantially reduced to the control level, but no inhibition was observed by treatment with normal control IgG (FIG. 4B, right).

INDUSTRIAL APPLICABILITY

According to the present invention, an anti-human aggrecanase antibody useful for the prophylaxis or treatment of arthritis is provided.

This application is based on US provisional patent application Ser. No. 61/891,087 (filing date: Oct. 15, 2013), the contents of which are incorporated in full herein by this reference.

TABLE 3

237-53 LCDR1
SEQ ID NO: 1
RSSQSILYSSNNNYLA 237-53 LCDR2
SEQ ID NO: 2
HTASARES 237-53 LCDR3
SEQ ID NO: 3
QQYYSVSI 237-53 HCDR1
SEQ ID NO: 4
GTFSSFAIS

TABLE 3-continued 237-53 HCDR2
SEQ ID NO: 5
GTFPIFGQANYAQKFQG 237-53 HCDR3
SEQ ID NO: 6
FSDWWEWQMDY 237-53 VL(kappa4)
SEQ ID NO: 7
DIVMTQSPDSLAVSLGERATINCRSSQSILYSSNNNYLAWYQQKPGQPPK
LLIHTASARESGVPDRFSGSGSGTDFTLTISSLQAEDVAVYYCQQYYSVS
ITFGQGTKVEIKRT 237-53 VH(VH1a)
SEQ ID NO: 8
QVQLVQSGAEVKKPGSSVKVSCKASGTFSSFAISWVRQAPGQGLEWMGGI
FPIFGQANYAQKFQGRVTITADESTSTAYMELSSLRSEDTAVYYCARFSD
WWEWQMDYWGQGTLVTVSS 237-53 epitope
SEQ ID NO: 9
YCEGRRTRF 237-53 epitope
SEQ ID NO: 10
GGKYCEGRRTRF 237-53 epitope
SEQ ID NO: 11
GKYCEGRRTRFR 237-53 epitope
SEQ ID NO: 12
KYCEGRRTRFRS 237-53 epitope
SEQ ID NO: 13
YCEGRRTRFRSC human ADAMTS4 cDNA sequence
SEQ ID NO: 14
GGGGAGAACCCACAGGGAGACCCACAGACACATATGCACGAGAGAGACAG
AGGAGGAAAGAGACAGAGACAAAGGCACAGCGGAAGAAGGCAGAGACAGG
GCAGGCACAGAAGCGGCCCAGACAGAGTCCTACAGAGGGAGAGGCCAGAG
AAGCTGCAGAAGACACAGGCAGGGAGAGACAAAGATCCAGGAAAGGAGGG
CTCAGGAGGAGAGTTTGGAGAAGCCAGACCCCTGGGCACCTCTCCCAAGC
CCAAGGACTAAGTTTTCTCCATTTCCTTTAACGGTCCTCAGCCCTTCTGA
AAACTTTGCCTCTGACCTTGGCAGGAGTCCAAGCCCCCAGGCTACAGAGA
GGAGCTTTCCAAAGCTAGGGTGTGGAGGACTTGGTGCCCTAGACGGCCTC
AGTCCCTCCCAGCTGCAGTACCAGTCCCATGTCCCAGACAGGCTCGCATC
CCGGGAGGGGCTTGGCAGGGCGCTGGCTGTGGGGAGCCCAACCCTGCCTC
CTGCTCCCCATTGTGCCGCTCTCCTGGCTGGTGTGGCTGCTTCTGCTACT
GCTGGCCTCTCTCCTGCCCTCAGCCCGGCTGGCCAGCCCCTCCCCCGGG
AGGAGGAGATCGTGTTTCCAGAGAAGCTCAACGGCAGCGTCCTGCCTGGC
TCGGGCGCCCCTGCCAGGCTGTTGTGCCGCTTGCAGGCCTTTGGGGAGAC
GCTGCTACTAGAGCTGGAGCAGGACTCCGGTGTGCAGGTCGAGGGGCTGA
CAGTGCAGTACCTGGGCCAGGCGCCTGAGCTGCTGGGTGGAGCAGAGCCT
GGCACCTACCTGACTGGCACCATCAATGGAGATCCGGAGTCGGTGGCATC
TCTGCACTGGGATGGGGAGCCCTGTTAGGCGTGTTACAATATCGGGGGG
CTGAACTCCACCTCCAGCCCCTGGAGGGAGGCACCCCTAACTCTGCTGGG
GGACCTGGGGCTCACATCCTACGCCGGAAGAGTCCTGCCAGCGGTCAAGG
TCCCATGTGCAACGTCAAGGCTCCTCTTGGAAGCCCCAGCCCCAGACCCC
GAAGAGCCAAGCGCTTTGCTTCACTGAGTAGATTTGTGGAGACACTGGTG
GTGGCAGATGACAAGATGGCCGCATTCCACGGTGCGGGCTAAAGCGCTA
CCTGCTAACAGTGATGGCAGCAGCAGCCAAGGCCTTCAAGCACCCAAGCA
TCCGCAATCCTGTCAGCTTGGTGGTGACTCGGCTAGTGATCCTGGGGTCA
GGCGAGGAGGGGCCCCAAGTGGGGCCCAGTGCTGCCCAGACCCTGCGCAG
CTTCTGTGCCTGGCAGCGGGGCCTCAACACCCCTGAGGACTCGGACCCTG
ACCACTTTGACACAGCCATTCTGTTTACCCGTCAGGACCTGTGTGGAGTC
TCCACTTGCGACACGCTGGGTATGGCTGATGTGGGCACCGTCTGTGACCC
GGCTCGGAGCTGTGCCATTGTGGAGGATGATGGGCTCCAGTCAGCCTTCA
CTGCTGCTCATGAACTGGGTCATGTCTTCAACATGCTCCATGACAACTCC
AAGCCATGCATCAGTTTGAATGGGCCTTTGAGCACCTCTCGCCATGTCAT
GGCCCCTGTGATGGCTCATGTGGATCCTGAGGAGCCCTGGTCCCCCTGCA
GTGCCCGCTTCATCACTGACTTCCTGGACAATGGCTATGGGCACTGTCTC
TTAGACAAACCAGAGGCTCCATTGCATCTGCCTGTGACTTTCCCTGGCAA
GGACTATGATGCTGACCGCCAGTGCCAGCTGACCTTCGGGCCCGACTCAC
GCCATTGTCCACAGCTGCCGCCGCCCGTGCTGCCCTCTGGTGCTCTGGC

TABLE 3-continued

```
CACCTCAATGGCCATGCCATGTGCCAGACCAAACACTCGCCCTGGGCCGA
TGGCACACCCTGCGGGCCCGCACAGGCCTGCATGGGTGGTCGCTGCCTCC
ACATGGACCAGCTCCAGGACTTCAATATTCCACAGGCTGGTGGCTGGGGT
CCTTGGGGACCATGGGGTGACTGCTCTCGGACCTGTGGGGGTGGTGTCCA
GTTCTCCTCCCGAGACTGCACGAGGCCTGTCCCCCGGAATGGTGGCAAGT
ACTGTGAGGGCCGCCGTACCCGCTTCCGCTCCTGCAACACTGAGGACTGC
CCAACTGGCTCAGCCCTGACCTTCCGCGAGGAGCAGTGTGCTGCCTACAA
CCACCGCACCGACCTCTTCAAGAGCTTCCCAGGGCCCATGGACTGGGTTC
CTCGCTACACAGGCGTGGCCCCCCAGGACCAGTGCAAACTCACCTGCCAG
GCCCAGGCACTGGGCTACTACTATGTGCTGGAGCCACGGGTGGTAGATGG
GACCCCCTGTTCCCCGGACAGCTCCTCGGTCTGTGTCCAGGGCCGATGCA
TCCATGCTGGCTGTGATCGCATCATTGGCTCCAAGAAGAAGTTTGACAAG
TGCATGGTGTGCGGAGGGGACGGTTCTGGTTGCAAGCAAGCAGTCAGGCTC
CTTCAGGAAATTCAGGTACGGATACAACAATGTGGTCACTATCCCCGCGG
GGGCCACCCACATTCTTGTCCGGCAGCAGGGAAACCCTGGCCACCGGAGC
ATCTACTTGGCCCTGAAGCTGCCAGATGGCTCCTATGCCCTCAATGGTGA
ATACACGCTGATGCCCTCCCCCACAGATGGTACTGCCTGGGGCAGTCA
GCTTGCGCTACAGCGGGGCCACTGCAGCCTCAGAGACACTGCTCAGGCCAT
GGGCCACTGGCCCAGCCTTTGACACTGCAAGTCCTAGTGGCTGGCAACCC
CCAGGACACACGCCTCCGATACAGCTTCTTCGTGCCCCGGCCGACCCCTT
CAACGCCACGCCCACTCCCCAGGACTGGCTGCACCGAAGAGCACAGATT
CTGGAGATCCTTCGGCGGCGCCCCTGGGCGGGCAGGAAATAACCTCACTA
TCCCGGCTGCCCTTTCTGGGCACCGGGGCCTCGGACTTAGCTGGGAGAAA
GAGAGAGCTTCTGTTGCTGCCTCATGCTAAGACTCAGTGGGGAGGGGCTG
TGGGCGTGAGACCTGCCCTCCTCTCTGCCCCTAATGCGCAGGCTGGCCCT
GCCCTGGTTTCCTGCCCTGGGAGGCAGTGATGGGTTAGTGGATGGAAGGG
GCTGACAGACAGCCCTCCATCTAAACTGCCCCCTCTGCCCTGCGGGTCAC
AGGAGGGAGGGGGAAGGCAGGGAGGGCCTGGGCCCCAGTTGTATTATT
AGTATTATTCACTTTTATTTAGCACCAGGGAAGGGGACAAGGACTAGGG
TCCTGGGGAACCTGACCCCTGACCCCTCCATAGCCCTCACCCTGGGGCTAG
GAAATCAGGGTGGTGGTGATAGGTATAAGTGGTGTGTGTATGCGTGTGT
GTGTGTGTGAAAATGTGTGTGCTTATGTATGAGGTACAACCTGTTCTG
CTTTCCTCTTCCTGAATTTATTTTTTGGGAAAAGAAAAGTCAAGGGTAG
GGTGGGCCTTCAGGGAGTGAGGATTATCTTTTTTTTTTTTCTTTCTTTC
TTTCTTTTTTTTTTTGAGACAGAATCTCGCTCTGTCGCCCAGGCTGGA
GTGCAATGGCACAATCTCGGCTCACTGCATCCTCCGCCTCCGGGTTCAA
GTGATTCTCATGCCTCAGCCTCCTGAGTAGCTGGGATTACAGGCTCCTGC
CACCACGCCCGGCTAATTTTTGTTTTGTTTTGTTTGGAGACAGAGTCTCG
CTATTGTCACCAGGGCTGGAATGATTTCAGCTCACTGCAACCTTCGCCAC
CTGGGTTCCAGCAATTCTCCTGCCTCAGCCTCCCGAGTAGCTGAGATTAT
AGGCACCTACCACCACGCCCGGCTAATTTTTGTATTTTTAGTAGAGACGG
GGTTTCACCATGTTGGCCAGGCTGGTCTCGAACTCCTGACCTTAGGTGAT
CCACTCGCCTTCATCTCCCAAAGTGCTGGGATTACAGGCGTGAGCCACCG
TGCCTGGCCACGCCCAACTAATTTTTGTATTTTTAGTAGAGACAGGGTTT
CACCATGTTGGCCAGGCTGCTCTTGAACTCCTGACCTCAGGTAATCGACC
TGCCTCGGCCTCCCAAAGTGCTGGGATTACAGGTGTGAGCCACCACGCC
GGTACATATTTTTAAATTGAATTCTACTATTTATGTGATCCTTTTGGAG
TCAGACATGATGGTTGCATCCTAACTCCATGTCTCTGAGCATTAGATTT
CTCATTTGCCAATAATAATACCTCCCTTAGAAGTTTGTTGTGAGGATTAA
ATAATGTAAATAAAGAACTAGCATAACACTCAAAAAAAAAAAAAAAAAA
AAAAAAAAAAAAAAAAAAAAAAAAAAAAAAAAAAAAAAAAAAAAAAAA
AAAAAAAAA human ADAMTS4 amino acid sequence
                                    SEQ ID NO: 15
MSQTGSHPGPGLAGRWLWGAQPCLLLPIVPLSWLVWLLLLLLASLLPSAR
LASPLPREEEIVFPEKLNGSVLPGSGAPARLLCRLQAFGETLLLELEQDS
GVQVEGLTVQYLGQAPELLGGAEPGTYLTGTINGDPESVASLHWDGGALL
GVLQYRGAELHLQPLEGGTPNSAGGPGAHILRRKSPASGQGPMCNVKAPL
GSPSPRPRRAKRFASLSRFVETLVVADDKMAAFHGAGLKRYLLTVMAAAA
KAFKHPSIRNPVSLVVTRLVILGSEEGPQVGPSAAQTLRSFCAWQPGLN
TPEDSDPDHFDTAILPTRQDLCGVSTCDTLGMADVGTVCDPARSCAIVED
DGLQSAFTAAHELGHVFNMLHDNSKPCISLNGPLSTSRHVMAPVMAHVDP
EEPWSPCSAPFITDFLDNGYGHCLLDKPEAPLHLPVTFPGKDYDADRQCQ
LTFGPDSPHCPQLPPPCAALWCSGHLNGHAMCQTKHSPWADGTPCGPAQA
CMGGRCLHMDQLQDFNIPQAGGWGPWGPWGDCSPTCGGGVQFSSRDCTRP
VPRNGGKYCEGRRTRFRSCNTEDCPTGSALTFREEQCAAYNHRTDLFKSF
PGPMDWVPRYTGVAPQDQCKLTCQAQALGYYYVLEPRVVDGTPCSPDSSS
VCVQGRCIHAGCDRIIGSKKKFDKCMVCGGDGSGCSKQSGSFRKFRYGYN
NVVTIPAGATHILVRQQGNPGHRSIYLALKLPDGSYALNGEYTLMPSPTD
VVLPGAVSLPYSGATAASETLSGHGPLAQPLTLQVLVAGNPQDTRLRYSF
FVPRPTPSTPRPTPQDWLHRRAQILEILRRRPWAGPK human ADAMTS5 cDNA sequence
                                    SEQ ID NO: 16
ATAAATTCATTGTTCCACCTCCTCGCATCTTCACAGCGCTCGCGCTGCTC
TCGGCGCTCGCAGCTGCCGACTGGGGATGACGGCGGGCAGGAGGAGACCG
CAGCCGAAGGGACACAGACACGCCGCTTCACCAGCTCGCCTCAGGCTGCC
CCCCTGCATTTTGTTTTAATTTTTACGGCTTTTTCCCCTCTCTTTCTTC
CCTTCCTCCTGGTCCCAGCAGAGCCAAGGAAACCCACAAAATAAGAAAGG
AAGTGGGCCCCGGAGCTTGGAACCTCCACAGCCGGCTTGTCCAGCGCAGC
GCGGGGCGGGAGGCTGCGCGCACCAGTTGCCAGCCCGGTGCGCGGTACC
TTTCCTTACTTTTCTTGAAACAGCGATCGTGCCTGCATTTGGTGGTTTTT
TGGTTTTTGTTTTTTTCCTTTTCCCGTATTTGCTGAATCTCCACTATCCG
ACTTTTTTTTTTTAATCTTTTCTTTCCCCCCCCCCCCCACCCCACCRCTTT
CTGGAGCACGAATCCAAACATTTTCCCAAGCAACAAAGAAAAGTTCGCAC
GCTGGCACCGCAGCCCGGACAGGCTGGCGCTGCTGCCGGGCCCCCTCCC
TCCGACACTTGACTCAATCCTGCAAGCAAGTGTGTGTGTCCCCATCCC
CCGCCCGTTAACTTCATAGCAAATAACAAATACCCATAAAGTCCCAGTC
GCGCAGCCCCTCCCCGCGGGCAGCGCACTATGCTGCTCGGGTGGGCGTCC
CTGCTGCTGTGCGCGGTTCCGCCTGCCCCTGGCCGCGGTCGGCCCCGCCGC
GACACCTGCCCAGGATAAAGCCGGGCAGCCTCCGACTGCTGCAGCAGCCG
CCCGACCCCGCCGGCGGCGAGGGGAGGAGGTGCAGGAGCGAGCCGAGCCT
CCCGGCCACCCGCACCCCCTGGCGCAGCGGCGCAGGAGCAAGGGGCTGGT
GCAGAACATCGACCAACTCTACTCCGGCGGCGGCAAGGTGGGCTACCTCG
TCTACGCGGGCGGCCGGAGGTTCCTCTTGGACCTGGAGCGAGATGGTTCG
GTGGGCATTGCTGGCTTCGTGCCCAGGAGGCGGATGAGGTGCGCCCTG
GCGCCACCGGAGCCACTGCTTCTATCGGGGCACAGTGGACGGTAGTCCCC
GCTCTCTGGCTGTCTTTGACCTCTGTGGGGGTCTCGACGGCTTCTTCGCG
GTCAAGCACGCGCGCTACACCCTAAAGCCACTGCTGCGCGGACCCTGGGC
GGAGGAGAAAAGGGGCGCGTGTACAGGGATGGGTCCGCACGGATCCTGC
ACGTCTACACCCGCGAGGGCTTCAGCTTCGAGGCCCTCCGCCGCGCGCC
AGCTGCGAAACCCCGCGTCCACACCGGAGGCCCACGAGCATGCTCCGGC
GCACAGCAACCCGAGCGGACGCGCAGCACTGGCCTCGCAGCTCTTGGACC
AGTCCGCTCTCTCGCCCGCTGGGGGCTCAGGACCGCAGACGTGGTGCCGG
CGGCGGCGCCGCTCCATCTCCCGGGCCCGCCAGGTGGCGTGCTTCTGGT
GGCTGACGCGTCCATGGCGCGGTTGTATGGCCGGGGCCTGCAGCATTACC
TGCTGACCCTGGCCTCCATCGCCAATAGGCTGTACAGCCATGCTAGCATC
GAGAACCACATCCGCCTGCCCGTGGTGAAGGTGGTGGTGCTAGGCGACAA
GGACAAGACCTGGAAGTGAGCAAGAACGCTGCCACCACACTCAAGAACT
TTTGCAAGTGGCAGCACCAACACAACCAGCTGGGAGATGACCATGAGGAG
CACTACGATGCAGCTATCCTGTTTACTCGGGAGGATTTATGTGGGCATCA
TTCATGTGACACCCTGGGAATGGCAGACGTTGGGACCATATGTTCTCCAG
AGCGCAGCTGCTGCTGTGATTGAAGCACGATGGCCTCCACGCAGCCTTCACT
GTGGCTCACGAAATCGGACATTTACTTGGCCTCTCCCATGACGATTCCAA
ATTCTGTGAAGAGACCTTTGGTTCCACAGAAGATAAGCGCTTAATGTCTT
CCATCCTTACCAGCATTGATGCATCTAAGCCCTGGTCCAAATGCACTTCA
GCCACCATCACAGAATTCCTGGATGATGGCCATGGTAACTGTTTGCTGGA
CCTACCACGAAAGCAGATCCTGGGCCCCGAAGAACTCCCAGGACAGACCT
ACGATGCCACCCAGCAGTGCAACCTGACATTCGGGCCTGAGTACTCCGTG
TGTCCCGGCATGGATGTCTGTGCTCGCCTGTGGTGTGCTGTGGTACGCCA
GGGCCAGTGGTCTGTCTGACCAAGAAGCTGCCTGCGGTGGAAGGGCAG
CTTGTGAAAGGGGAGAATCTGCCTGCAGGGCAAATGTGTGGACAAAACC
AAGAAAAAATATTATTCAACGTCAAGCCATGGCAACTGGGGATCTTGGGG
ATCCTGGGGCCAGTGTTCTCGCTCATGTGGAGGAGGAGTGCAGTTTGCCT
ATGCTCACTGTAATAACCCTGCTCCCAGAAACAACGGACGCTACTGCACA
GGGAAGAGGGCCATCTACCGCTGCAGTCTCATGCCCTGCCCACCCAA
TGGTAAATCATTTCGTCATGAACAGTGTGAGGCAAAAATGGCTATCAGT
CTGATGCAAAAGGAGTCAAAACTTTTGTGGAATGGGTTCCCAAATATGCA
GGTGTCCTGCCAGCGGATGTGTGCAAGCTGACCTGCAGAGCCAAGGGCAA
TGGCTACTATGTGGTATTTTCTCCAAAGGTGACCGATGGCACTGAATGTA
GGCTGTACAGTAATTCCGTCTGCGTCCGGGGGAAGTGTGTGAGAACTGGC
TGTGACGGCATCATTGGCTCAAAGCTGCAGTATGACAAGTGCGGAGTATG
TGGAGGAGCAACTCCAGCTGTACAAAGATTGTTGAACCTTTAATAAGA
AAAGTAAGGGTTACACTGACGTGGTGAGGATTCCTGAAGGGGCAACCCAC
ATAAAAGTTCGACAGTTCAAAGCCAAAGACCAGACTAGATTCACTGCCTA
TTTAGCCCTGAAAAAGAAAACGGTGAGTACCTTATCAATGGAAAGTACA
TGATCTCCACTTCAGAGACTATCATTGACATCAATGGAAGTGCATGAAC
TATAGCGGTTGGAGCACAGGGATGACTTCCTGCATGGCATGGGCTACTC
TGCCCACGAAGGAAATTCTAATAGTGCAGATTCTTGCAACAGACCCCACTA
AACCATTAGATGTCCGTTATAGCTTTTTTGTTCCCAAGAAGTCCACTCCA
AAAGTAAACTCTGTCACTAGTCATGGCAGCAATAAAGTGGGATCACACAC
TTCGCAGCCGCAGTGGGTCACGGGCCCATGGCTGCCTGCCTTAGGACCT
GTGACCAGGTTGGCACACCAGAACGGTGCAGTGCCAGGATGGAAACCGG
AAGTTAGCAAAGGATGTCCTCTCTCCCAAAGGCCTTCTGCGTTTAAGCA
ATGCTTGTTGAAGAAATGTTAGCCTGTGGTTATGATCTTATGCACAAAGA
TAACTGGAGGATTCAGCACTGATCAGTCGTGGTGAACAGGAGGTCTACC
TAACGCACAGAAAGTCATGCTTCAGTGACATTGTCAACAGGAGTCCAATT
ATGGGCAGAATCGCTCTCTGTGACCAAAAGAGGATGTGCACTGCTTCAC
GTGACAGTGGTGACCTTGCAATATAGAAAACTTGGGAGTTATTGAACAT
CCCCTGGGCTTACAAGAAACACTGATGAATGTAAAATCAGGGGACATTG
AAGATGGAGAACTGTCTCCCCCTTGTCACCTACCTCTGATAGAATGTCT
TTAATGGTATCATAATCATTTTCACCCATAATACACAGTAGCTTCTTCTT
ACTGTTTGTAAATACATTCTCCCTTGGTATGTCACTTTATATCCCCTGGT
TCTATTAAAATATCCATATATATTTCTATAAAAAAGTGTTTGACCAAGA
TAGGTCTGCAGCTATTTCAACTTCCTTCCGTTTCCAGAAAGAGCTGTGGA
TATTTACTGGAAATTAAGACTTGCTGCTGTTTAATAAGATGTAGTAT
ATTTTCTGACTACAGGAGATAAAATTTCAGTCAAAAAACCATTTTGACAG
CAAGTATCTTCTGAGAAATTTTGAAAAGTAAATAGATCTCAGTGTATCTA
GTCACTTAAATACATACACGGGTTCATTTACTTAAACCTTTGACTGCCTG
```

TABLE 3-continued

```
TATTTTTTTCAGGTAGCTAGCCAAATTAATGCATAATTTCAGATGTAGAA
GTAGGGTTTGCGTGTGTGTGTGATCATACTCAAGAGTCTAAAAACTAG
TTTCCTTGTGTTGGAAATTTAAAAGGAAAAAAATCGTATTTCACTGTGTT
TTCAATTTATATTTTCACAACTACTTTCTCTCTCCAGAGCTTTCATCTGA
TATCTCACAATGTATGATATACGTACAAAACACACAGCAAGTTTTCTATC
ATGTCCAACACATTCAACACTGGTATACCTCCTACCAGCAAGCCTTTAAA
ATGCATTTGTGTTTGCTTATTTGTTTTGTTCAAGGGTTCAGTAAGACCTA
CAATGTTTTGTATTTCTTGACTTATTTTATTAGAAACATTAAAGATCACT
TGGTAGTTAGCCACATTGAGAAGTGGTTATCATTGTTAATGTGGTTAATG
CCAAAAAGTGGTTAATATTAATAAGACTGTTTCCACACCATAGGCAATAA
TTTCTTAATTTAAAAAATCTAAGTATATTCCTATTGTACTAAATATTTTT
CCCAACTGGAAAGCACTTGATTGTACCCGTAAGTGTTTGAGTGATGACAT
GTGATGATTTTCAGAAAGTTGTTGTTTTTGTTTCCATAGCCTGTTTAAGT
AGGTTGTAAGTTTGAATAGTTAGACATGGAAATTATTTTATAAGCACACA
CCTAAAGATATCTTTTTAGATGATAAAATGTACACCCCCCCATCACCAAC
CTCACAACTTAGAAAATCTAAGTTGTTTGATTTCTTTGGGATTTCTTTTG
TTGTGAAACACTGCAAAGCCAATTTTTCTTTATAAAAATTCATAGTAATC
CTGCCAAATGTGCCTATTGTTAAAGATTTGCATGTGAAGATCTTAGGGAA
CCACTGTTTGAGTTCTACAAGCTCATGAGAGTTTATTTTTATTATAAGAT
GTTTTTAATATAAAAGAATTATGTAACTGATCACTATATTACATCATTTC
AGTGGGCCAGGAAAATAGATGCTTGCTGTTTCAGTATTTTCTTAAGAA
ATTGCTTTTAAAACAAATAATTGTTTTACAAAACCAATAATTATCCTTTG
AATTTTCATAGACTGACTTTGCTTTTGACGTAGAAATTTTTTTCTCAAT
AAATTATCACTTTGAGAAATGAGGCCTGTACAAGGCTGATAACCTATATG
TGATGAGATCACCCAATGCCAAGGGCAGAAAGCAAACCTAGTTAAATAG
GTGAGAAAAAAATAATAATCCCAGTGCATTTGTCTGTGCAAAGAGAAT
TAGGAGAGAGGTTAATGTTACTTTTTTCCATTTTGGAAATAATTTTAATC
AAGTAACTCAAATGTGACAAAATTTATTTTTATTTTTTGTGGTTATATTC
CCAACAACATTAAAAATACTCGAGCATAAATGTAGTTGTCTCCTACTC
TGCTTCTCTTACTATACTCATACATTTTTAATATGGTTTATCAATGATTC
ATGTTTCCCTCAAATAGTGATGGTTTACACCTGTCATGGAAACAATCCTA
GAGAGCTCAGAGCAATTAAACCACTATTCCATGCTTTTAAGTAGTTTTCT
CCACCTTTTCTTATGAGTCTCACTAGATTGACTGAGGAATGTATGTCTA
AATTCCTGGAGAAGATGATATGGATTGGAAACTGAAATTCAGAGAAATGG
AGTGTTCAATAGATACCACGAATTGTGAACAAAGGGAAAATTCTATACAA
CTCAATCTAAGTCAGTCCACTTTGACTTCGTACTGTCTTTCACCTTTCCA
TTGTTGCATCTTGAATTTTTTAAAATGTCTAGAATTCAGGATGCTAGGGG
CTACTTCTTTAAAAAAAAAAAAAAAGAATTCGTCTGAAAATGCTCAG
GTTTGTAAGAATCTAATCTCACTTACATAACTAAGCACTCCATAATAAGT
TTTATTAAGTACAAAGGGAGCCAGAAAAATGACATTTATTTCTTCTAGA
TCAGAAAAATTTAAATTAAGCCCTGCCTTGCTGTTTAGAAATATGTGGGC
ATTGTTATAATTTATTCAATAAATTTATGTTCCTTTGCCTTCCTGTGGAA
ACAGTTTTATCCCACTAAACTAGGAATTAGGGGATAAATCACAAACAAAA
AAAAAGTTGCAGCACTGAAAAAAGTAATTTATTGTTTTGCAACTGGTA
TGTGAATTTGTGTGATAAAATTATTTATTCTTATTTAACAAAAATATGTT
CAAATTTTCTATATTTAAAATGTTTTGCTGTTGTCCTACTTTTTAATTT
ATGCTTCATGTTTGTGTATAAAGTACACTTTTACACTTTGTGAGTTTACA
TAATATACAGCACTGGTTGCTTTTGTATTTTTTACAGAAAGCTTTCTGT
GTGAAGCAGGTGTATATGTATATATTCCTCATGTATTCTTATTCTGATAC
TATCATTTTCTTTCCAAAGTATTTTTAATCTGTCATGACCAATAGTGTT
CATTACTTGTGCCTATGATAATAGGTTTTTTACATCACATTAACACTATT
TTTCCAAGTCACAAATAAGAAAAACACTTATTCAATGAAACAAGGTGCA
AGTTTTAAATTTGGGTACACAAATAGCCTAGAACCTTCCTACAGACGCTA
AGACACAGCCAATAATCAGATTCCTTCACTTCATCCAGAAACTTGGACAA
GTCGATATTGATGTATTAGATGAAAGTTGTCTACACAACTTCTGAGGG
ATACAAACGATAATAAAACCAAATGTTGTCTGTTTCTCCTTTAGAAACAC
CTCCTAAAATTAATATCATTTAGTCTCTAGTGTCTGTAGGATTCTACAGA
TGAGCACAAATGATTGGGTTGTATAACAAATGCTAATAGTCATAACTG
TTTCTACAAATATGGGGTGTCCATTAAGAGAATGTGATGTTTTTCCTACTG
CTGTTGAATCCCATGGGGTGATTATAGGCTTGAAATAGGCAGAGTCACC
TCTGATGACATCAGCTTGCCTCTGTGATTTCACAGTCTGATCCTGGCAAC
AAGACAAAGCACCCTTGGACACACAGCCAATCTCTGGTTGTGATATTTCC
CCATTGATTCCTTTCCTTGTTAACAAGGTCATTTTAATTGTTTCAGGTGAGG
ACAGCACCAGATTCAAAGTCCAGAATTTGTGCTGTTACATAGAGTTCAC
ACTGTCAAATAACATTGAATTTAATAATGATCAAATTTTTCTAGTAGTCT
TTGGCAGAGTGTATAATCTCATTGGCATGATTGGTGAATATTACTAATCT
```

| | |
|---|---|
| | CTTTATAATGAAAGATGCTTTACAAATACCTTATATTTGCTAACATTTCA |
| | AAACTACTAAATAAATGAAATAGCCATGTGTACAGAAATGGTCATTTAAA |
| | GCTTTAATAGAACCAAATTCAAGACAATGTATCATTTAGACACACAGAAA |
| 5 | AGGAACTTCGTATGTTTTCCCTATTATTTTTCTCATTTGCCAACAATCTAT |
| | AGTTTTAGGTTATCAAACAGATAGATCAACTTAACTGGCTAGTACATTGA |
| | AAAATCTTCCTAAGAATCCTTTGTTAGCATAATCTATAGAGATAATTTCT |
| | CAAATTATATCATCATGATGCATATAAACTCTATAATGTATAATTGTGTT |
| | TCATTTATTTAATGTATGAGAACATATTGAAATACAAAACCATGCATTAG |
| | CCAAAAAATTGGAATACAGGTAGTGTTCAGATCAGCAAAACATTCAGTCT |
| 10 | GGTAAATGCCTGCCTGGGGCTATGATATCATTCTCAATGCAGGTTTTATG |
| | GAAAAACTAAAAGAATATGTTGTTAGATGATGTTGGTTTTGAAAAAAAAA |
| | AGACATTAACATACACATTAGTTAGCCCAGTTAATTGCATTCTACTAATA |
| | TAGTTGCACATTAGCAATAATTTTGCTGTCTCTGGTCTTTATTTGTGGC |
| | TTCAACTAACTGGACCATGTGGACTGTAAAGGTCAAATGGAAAAAACGAG |
| | CAGTGGCCCCTCATCCTGTAAGGTACTGCTACATCAGAGTGACCTAAAAG |
| 15 | TCTAACACTGTGAGGAAAACTGTGATTTGTAGGAAAAAAAAAAAAAACAA |
| | ATAAAAAACAGGGCATGCTTTTTAATTTTTTTCCACTTTCCTTTGGCACA |
| | CCCAATGAACAATTCTAATTTTTATTGAGGTGCTAACTCTTTCGTGACC |
| | GACTGTCAAATGTGGTATTTTTGAGTTACTATTTTTCTACATGATTTTAC |
| | AGTTTGCAAGAAAGACCTCTAAGCTTTGTGTCACGGTAGGGCACAACTTG |
| | ATACTCAAATTTGAAAAATAAGCACATCCAATGATTGTTTTGACCAACA |
| 20 | GTGGTCAGTGACGTAAACTGCATGTGCATCTGAGGACATTTAAGGGGTCA |
| | TTAAAATTTGAGGAGCATCAGGCCGGAGTAGCAGACTTTTAGATGAGTCA |
| | TATTTCAGCATTCACTAAGTCCTCAGCATTCCATTCAAACTGTCGTGTAT |
| | ATTTGGCCTGATTTTTTTCAAGCTTTGCAATAATTTATGTTATTGGTAA |
| | ACACTTGGTACTATATCTCAGCCTTTTCTTTAACAACTCACAATATATT |
| | AGAAACACGTCTACCTATACTGAGAGTATATTTACAATAGAAGAACATAC |
| | TGTATGTGACTTTGTAAAGCTAGACTTTTGATTAAGAAATATATAATCTC |
| 25 | TGGATGCTATTTTTGCATTATACACTCAGGCACAACGTAAACCTTGATGG |
| | CTCATCTTGCTACAATTACGAGTTGAAAAACACTACTTACGTATTTGTAT |
| | GACCTATTAGTCAGAGGAAATCATACATATGCTTTGTAAATAGACTTTGC |
| | AGATAACTAAATAGACTGAAGAAATATGTTGCATTTGATAGAAGCAATTG |
| | CATAAATATTTGGTTCTATATTAGAGCTGTGAGTAAAGTCAAGTAATA |
| | AACCTAAGTAGGTATAACAGATTTTTAAACCTTGAAACTTGCTTTGATGG |
| 30 | TAGAGAAAATCATTGAAGATTTACATACTGTATATAAGATGAAAATGTA |
| | CGCTGCTTATTACCCTCAATTTTCCAGAAGCAATGGTATATAATGCAGTT |
| | GAAAAACCAAAAATCTTGGAAAACTAAGACGGGTCTTGTTTAAAATGTCT |
| | CTCAGCTTTGCAACCTTCAAATCTTAATCAACTATTTAAAGCATTACTG |
| | TGTCTTGTAGCCTGCATTCCACAACAGCTCTGTTATTCAGGTAAAAGACT |
| | TGAACTGAGCCGTTTGGGACCTATACTGTAATATTTTCATTGAGGAACAA |
| 35 | TATCCTATTTTGTAAAGCATTTCCCTATGTGTGACTTTAAACTGTAAAAT |
| | TAAACACTGCTTTTGTGGGTTCAGTGGGCATAATAAATATAAATTGTAAA |
| | CTAGGTTAAAGTA | human ADAMTS5 amino acid sequence
SEQ ID NO: 17

MLLGWASLLLCAFRLPLAAVGPAATPAQDKAGQPPTAAAAAQPRRRQGEE
VQERAEPPGHPHPLAQRRRSKGLVQNIDQLYSGGGKVGYLVYAGGRRFLL
DLERDGSVGIAGFVPAGGGTSAPWRHRSHCFYRGTVDGSPRSLAVFDLCG
GLDGFFAVKHARYTLKPLLRGPWAEEEKGRVYGDGSARILHVYTREGFSF
EALPPRASCETPASTPEAHEHAPAHSNPSGRAALASQLLDQSALSPAGGS
GPQTWWRRRRSISRARQVELLLVADASMARLYGRGLQHYLLTLASIANR
LYSHASIENHIRLAVVKVVVLGDKDKSLEVSKNAATTLKNFCKWQHQHNQ
LGDDHEEHYDAAILFTREDLCGHHSCDTLGMADVGTICSPERSCAVIEDD
GLHAAFTVAHEIGHLLGLSHDDSKFCEETFGSTEDKRLMSSILTSIDASK
PQSKCTSATITEFLDDGHGNCLLDLPRKQILGPEELPGQTYDATQQCNLT
FGPEYSVCPGMDVCARLWCAVVRQGQMVCLTKKLPAVEGTPCGKGRICLQ
GKCVDKTKKKYYSTSSHGNWGSWGSWGQCSRSCGGGVQFAYRHCNNPAPR
NNGRYCTGKRAIYRSCSLMPCPPNGKSFRHEQCEAKNGYQSDAKGVKTFV
EWVPKYAGVLPADVCKLTCRAKGRGYYVVFSPKVTDGTECRLYSNSVCVR
GKCVRTGCDGIIGSKLQYDKCGVCGGDNSSCTKIVGTFNKKSKGYTDVVR
IPEGATHIKVRQFKAKDQTRFTAYLALKKKNGEYLINGKYMISTSETIID
INGTVMNYSGWSHRDDFLHGMGYSATKEILIVQILATDPTKPLDVRYSFF
VPKKSTPKVNSVTSHGSNKVGSHTSQPQWVTGPWLACSRTCDTGWHTRTV
QCQDGNRKLAKGCPLSQRPSAFKQCLLKKC

The invention claimed is:

1. An antibody comprising a light chain variable region and a heavy chain variable region,
   wherein the light chain variable region comprises: CDR1 comprising the amino acid sequence of SEQ ID NO: 1; CDR2 comprising the amino acid sequence of SEQ ID NO: 2; and CDR3 comprising the amino acid sequence of SEQ ID NO: 3, and
   wherein the heavy chain variable region comprises: CDR1 comprising the amino acid sequence of SEQ ID NO: 4; CDR2 comprising the amino acid sequence of SEQ ID NO: 5; and CDR3 comprising the amino acid sequence of SEQ ID NO: 6, wherein the antibody specifically binds human ADAMTS4.

2. The antibody according to claim 1,
   wherein the light chain variable region comprises the amino acid sequence of SEQ ID NO: 7, and
   wherein the heavy chain variable region comprises the amino acid sequence of SEQ ID NO: 8.

3. The antibody according to claim 1, wherein the antibody inhibits aggrecanase activity of the human aggrecanase.

4. The antibody according to claim 1, wherein the antibody further inhibits aggrecanase activity of human ADAMTS5.

5. The antibody according to claim 1,
   wherein the antibody binds to an epitope of a human aggrecanase, and
   wherein the epitope consists of 20 or less amino acid residues and comprises the amino acid sequence of SEQ ID NO: 9.

6. The antibody according to claim 5, wherein the epitope consists of an amino acid sequence selected from the group consisting of SEQ ID NOs: 9-13.

7. A pharmaceutical composition comprising the antibody according to claim 1.

* * * * *

SEQUENCE LISTING

<160> NUMBER OF SEQ ID NOS: 58

<210> SEQ ID NO 1
<211> LENGTH: 16
<212> TYPE: PRT
<213> ORGANISM: Artificial Sequence
<220> FEATURE:

```
<223> OTHER INFORMATION: Synthetic Sequence

<400> SEQUENCE: 1

Arg Ser Ser Gln Ser Ile Leu Tyr Ser Ser Asn Asn Asn Tyr Leu Ala
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 2

His Thr Ala Ser Ala Arg Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 3

Gln Gln Tyr Tyr Ser Val Ser Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 4

Gly Thr Phe Ser Ser Phe Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 5

Gly Ile Phe Pro Ile Phe Gly Gln Ala Asn Tyr Ala Gln Lys Phe Gln
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 6

Phe Ser Asp Trp Trp Glu Trp Gln Met Asp Tyr
1               5                   10

<210> SEQ ID NO 7
<211> LENGTH: 114
<212> TYPE: PRT
<213> ORGANISM: Artificial Sequence
```

```
<220> FEATURE:
<223> OTHER INFORMATION: Synthetic Sequence

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Leu Tyr Ser
            20                  25                  30

Ser Asn Asn Tyr Leu Ala Trp Tyr Gln Gln Lys Pro Gly Gln Pro
        35                  40                  45

Pro Lys Leu Leu Ile His Thr Ala Ser Ala Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Val Ser Ile Thr Phe Gly Gln Gly Thr Lys Val Glu Ile Lys
            100                 105                 110

Arg Thr

<210> SEQ ID NO 8
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Ala Ile Ser Trp Val Arg Gln Ala Pro Gly Gln Gly Leu Glu Trp Met
        35                  40                  45

Gly Gly Ile Phe Pro Ile Phe Gly Gln Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Ser Asp Trp Trp Glu Trp Gln Met Asp Tyr Trp Gly Gln
            100                 105                 110

Gly Thr Leu Val Thr Val Ser Ser
        115                 120

<210> SEQ ID NO 9
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 9

Tyr Cys Glu Gly Arg Arg Thr Arg Phe
1               5

<210> SEQ ID NO 10
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 10

Gly Gly Lys Tyr Cys Glu Gly Arg Arg Thr Arg Phe
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 11

Gly Lys Tyr Cys Glu Gly Arg Arg Thr Arg Phe Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 12

Lys Tyr Cys Glu Gly Arg Arg Thr Arg Phe Arg Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 13

Tyr Cys Glu Gly Arg Arg Thr Arg Phe Arg Ser Cys
1               5                   10

<210> SEQ ID NO 14
<211> LENGTH: 4410
<212> TYPE: DNA
<213> ORGANISM: Homo sapiens

<400> SEQUENCE: 14
ggggagaacc cacagggaga cccacagaca catatgcacg agagagacag aggaggaaag      60
agacagagac aaaggcacag cggaagaagg cagagacagg gcaggcacag aagcggccca     120
gacagagtcc tacagaggga gaggccagag aagctgcaga agacacaggc agggagagac     180
aaagatccag gaaaggaggg ctcaggagga gagtttggag aagccagacc cctgggcacc     240
tctcccaagc ccaaggacta agttttctcc atttccttta acggtcctca gcccttctga     300
aaactttgcc tctgaccttg gcaggagtcc aagcccccag gctacagaga ggagctttcc     360
aaagctaggg tgtggaggac ttggtgccct agacggcctc agtccctccc agctgcagta     420
ccagtgccat gtcccagaca ggctcgcatc ccggaggggg cttggcaggg cgctggctgt     480
ggggagccca accctgcctc ctgctcccca ttgtgccgct ctcctggctg gtgtggctgc     540
ttctgctact gctggcctct ctcctgccct cagcccggct ggccagcccc ctcccccggg     600
aggaggagat cgtgtttcca gagaagctca acggcagcgt cctgcctggc tcggcgcccc     660
ctgccaggct gttgtgccgc ttgcaggcct ttgggaagac gctgctacta gagctggagc     720
```

```
aggactccgg tgtgcaggtc gaggggctga cagtgcagta cctgggccag gcgcctgagc      780
tgctgggtgg agcagagcct ggcacctacc tgactggcac catcaatgga gatccggagt      840
cggtggcatc tctgcactgg gatggggag ccctgttagg cgtgttacaa tatcgggggg       900
ctgaactcca cctccagccc ctggaggag gcaccctaa ctctgctggg ggacctgggg        960
ctcacatcct acgccggaag agtcctgcca gcggtcaagg tcccatgtgc aacgtcaagg     1020
ctcctcttgg aagcccagc cccagacccc gaagagccaa gcgctttgct tcactgagta      1080
gatttgtgga gacactggtg gtggcagatg acaagatggc cgcattccac ggtgcgggc      1140
taaagcgcta cctgctaaca gtgatggcag cagcagccaa ggccttcaag cacccaagca    1200
tccgcaatcc tgtcagcttg gtggtgactc ggctagtgat cctggggtca ggcgaggagg    1260
ggccccaagt ggggcccagt gctgcccaga ccctgcgcag cttctgtgcc tggcagcggg    1320
gcctcaacac ccctgaggac tcggaccctg accactttga cacagccatt ctgtttaccc    1380
gtcaggacct gtgtggagtc tccacttgcg acacgctggg tatggctgat gtgggcaccg    1440
tctgtgaccc ggctcggagc tgtgccattg tggaggatga tgggctccag tcagccttca    1500
ctgctgctca tgaactgggt catgtcttca acatgtccca tgacaactcc aagccatgca    1560
tcagtttgaa tgggcctttg agcacctctc gccatgtcat ggcccctgtg atggctcatg    1620
tggatcctga ggagccctgg tccccctgca gtgcccgctt catcactgac ttcctggaca    1680
atggctatgg gcactgtctc ttagacaaac cagaggctcc attgcatctg cctgtgactt    1740
tccctggcaa ggactatgat gctgaccgcc agtgccagct gaccttcggg cccgactcac    1800
gccattgtcc acagctgccg ccgccctgtg ctgccctctg gtgctctggc cacctcaatg    1860
gccatgccat gtgccagacc aaacactcgc cctgggccga tggcacaccc tgcgggcccg    1920
cacaggcctg catgggtggt cgctgcctcc acatggacca gctccaggac ttcaatattc    1980
cacaggctgg tggctgggt ccttggggac catggggtga ctgctctcgg acctgtgggg    2040
gtggtgtcca gttctcctcc cgagactgca cgaggcctgt cccccggaat ggtggcaagt    2100
actgtgaggg ccgccgtacc cgcttccgct cctgcaacac tgaggactgc ccaactggct    2160
cagccctgac cttccgcgag gagcagtgtg ctgcctacaa ccaccgcacc gacctcttca    2220
agagcttccc agggcccatg gactgggttc ctcgctacac aggcgtggcc cccaggacc     2280
agtgcaaact cacctgccag gcccaggcac tgggctacta ctatgtgctg gagccacggg    2340
tggtagatgg gaccccctgt tccccggaca gctcctcggt ctgtgtccag ggccgatgca    2400
tccatgctgc tctgtgatcgc atcattggct ccaagaagaa gtttgacaag tgcatggtgt    2460
gcggagggga cggttctggt tgcagcaagc agtcaggctc cttcaggaaa ttcaggtacg    2520
gatacaacaa tgtggtcact atcccgcgcg ggggccaccca cattcttgtc cggcagcagg    2580
gaaaccctgg ccaccggagc atctacttgg ccctgaagct gccagatggc tcctatgccc    2640
tcaatggtga atacacgctg atgccctccc ccacagatgt ggtactgcct ggggcagtca    2700
gcttgcgcta cagcggggcc actgcagcct cagagacact gtcaggccat gggccactgg    2760
cccagccttt gacactgcaa gtcctagtgg ctggcaaccc ccaggacaca cgcctccgat    2820
acagcttctt cgtgccccgg ccgacccctt caacgccacg ccccactccc caggactggc    2880
tgcaccgaag agcacagatt ctggagatcc ttcggcggcg cccctgggcg ggcaggaaat    2940
aacctcacta tccggctgc cctttctggg caccgggcc tcggacttag ctgggagaaa     3000
gagagagctt ctgttgctgc ctcatgctaa gactcagtgg ggaggggctg tgggcgtgag    3060
```

```
acctgcccct cctctctgcc ctaatgcgca ggctggccct gccctggttt cctgccctgg      3120
gaggcagtga tgggttagtg gatggaaggg gctgacagac agccctccat ctaaactgcc      3180
ccctctgccc tgcgggtcac aggagggagg gggaaggcag ggagggcctg ggccccagtt      3240
gtatttattt agtatttatt cacttttatt tagcaccagg gaaggggaca aggactaggg      3300
tcctggggaa cctgacccct gaccctcat agccctcacc ctggggctag gaaatccagg      3360
gtggtggtga taggtataag tggtgtgtgt atgcgtgtgt gtgtgtgtga aaatgtgtgt      3420
gtgcttatgt atgaggtaca acctgttctg cttttcctctt cctgaatttt attttttggg      3480
aaaagaaaag tcaagggtag ggtgggcctt cagggagtga gggattatct tttttttttt      3540
ttctttcttt ctttcttttt ttttttgag acagaatctc gctctgtcgc ccaggctgga      3600
gtgcaatggc acaatctcgg ctcactgcat cctccgcctc ccgggttcaa gtgattctca      3660
tgcctcagcc tcctgagtag ctgggattac aggctcctgc caccacgccc ggctaatttt      3720
tgttttgttt tgtttggaga cagagtctcg ctattgtcac cagggctgga atgatttcag      3780
ctcactgcaa ccttcgccac ctgggttcca gcaattctcc tgcctcagcc tcccgagtag      3840
ctgagattat aggcacctac caccacgccc ggctaatttt tgtattttta gtagagacgg      3900
ggtttcacca tgttggccag gctggtctcg aactcctgac cttaggtgat ccactcgcct      3960
tcatctccca agtgctggg attacaggcg tgagccaccg tgcctggcca cgcccaacta      4020
atttttgtat ttttagtaga cagggttt caccatgttg gccaggctgc tcttgaactc      4080
ctgacctcag gtaatcgacc tgcctcggcc tcccaaagtg ctgggattac aggtgtgagc      4140
caccacgccc ggtacatatt ttttaaattg aattctacta tttatgtgat ccttttggag      4200
tcagacagat gtggttgcat cctaactcca tgtctctgag cattagattt ctcatttgcc      4260
aataataata cctcccttag aagtttgttg tgaggattaa ataatgtaaa taagaactca      4320
gcataacact caaaaaaaaa aaaaaaaaa aaaaaaaaa aaaaaaaaa aaaaaaaaa          4380 aaaaaaaaaa aaaaaaaaaa aaaaaaaaaa                                      4410
```

<210> SEQ ID NO 15
<211> LENGTH: 837
<212> TYPE: PRT
<213> ORGANISM: Homo sapiens

<400> SEQUENCE: 15

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
```

```
            130                 135                 140
Asp Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
                180                 185                 190

Met Cys Asn Val Lys Ala Pro Leu Gly Ser Ser Pro Arg Pro Arg
            195                 200                 205

Arg Ala Lys Arg Phe Ala Ser Leu Ser Arg Phe Val Glu Thr Leu Val
        210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
            340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
        435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Val Gln Phe Ser Ser
    530                 535                 540

Arg Asp Cys Thr Arg Pro Val Pro Arg Asn Gly Gly Lys Tyr Cys Glu
545                 550                 555                 560
```

Gly Arg Arg Thr Arg Phe Arg Ser Cys Asn Thr Glu Asp Cys Pro Thr
            565                 570                 575

Gly Ser Ala Leu Thr Phe Arg Glu Glu Gln Cys Ala Ala Tyr Asn His
            580                 585                 590

Arg Thr Asp Leu Phe Lys Ser Phe Pro Gly Pro Met Asp Trp Val Pro
            595                 600                 605

Arg Tyr Thr Gly Val Ala Pro Gln Asp Gln Cys Lys Leu Thr Cys Gln
            610                 615                 620

Ala Gln Ala Leu Gly Tyr Tyr Val Leu Glu Pro Arg Val Val Asp
625                 630                 635                 640

Gly Thr Pro Cys Ser Pro Asp Ser Ser Val Cys Val Gln Gly Arg
            645                 650                 655

Cys Ile His Ala Gly Cys Asp Arg Ile Ile Gly Ser Lys Lys Lys Phe
            660                 665                 670

Asp Lys Cys Met Val Cys Gly Gly Asp Gly Ser Gly Cys Ser Lys Gln
            675                 680                 685

Ser Gly Ser Phe Arg Lys Phe Arg Tyr Gly Tyr Asn Asn Val Val Thr
    690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
            725                 730                 735

Ala Leu Asn Gly Glu Tyr Thr Leu Met Pro Ser Pro Thr Asp Val Val
            740                 745                 750

Leu Pro Gly Ala Val Ser Leu Arg Tyr Ser Gly Ala Thr Ala Ala Ser
            755                 760                 765

Glu Thr Leu Ser Gly His Gly Pro Leu Ala Gln Pro Leu Thr Leu Gln
            770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
            805                 810                 815

Trp Leu His Arg Arg Ala Gln Ile Leu Glu Ile Leu Arg Arg Pro
            820                 825                 830

Trp Ala Gly Arg Lys
        835

<210> SEQ ID NO 16
<211> LENGTH: 9663
<212> TYPE: DNA
<213> ORGANISM: Homo sapiens

<400> SEQUENCE: 16
ataaattcat tgttccacct cctcgcatct tcacagcgct cgcgctgctc tcggcgctcg      60
cagctgccga ctggggatga cggcgggcag gaggagaccg cagccgaagg gacacagaca     120
cgccgcttca ccagctcgcc tcaggctgcc ccctgcatt tttgttttaa tttttacggc      180
tttttcccct ctctttcttc ccttcctcct ggtcccagca gagccaagga aacccacaaa     240
ataagaaagg aagtgggccc cggagcttgg aacctccaca gccggcttgt ccagcgcagc     300 gcggggggcgg gaggctgcgc gcaccagttg ccagcccggt gcgcggtacc tttccttact     360
tttcttgaaa cagcgatcgt gcctgcattt ggtggttttt tggttttgt ttttttcctt     420 ttcccgtatt tgctgaatct ccactatccg acttttttt tttaatcttt tctttccccc      480

-continued

```
cccccccacc ccacctctttt ctggagcacg aatccaaaca ttttcccaag caacaaagaa      540
aagttcgcac gctggcaccg cagcccggac aggctggcgc tgctgccggg ccccccctccc     600 tccgacactt gactcaatcc tgcaagcaag tgtgtgtgtg tccccatccc ccgccccgtt      660
aacttcatag caaataacaa atacccataa agtcccagtc gcgcagcccc tccccgcggg      720
cagcgcacta tgctgctcgg gtgggcgtcc ctgctgctgt gcgcgttccg cctgcccctg      780
gccgcggtcg gccccgccgc gacacctgcc caggataaag ccgggcagcc tccgactgct      840
gcagcagccg cccagccccg ccggcggcag ggggaggagg tgcaggagcg agccgagcct      900 cccgccacc cgcacccccct ggcgcagcgg cgcaggagca aggggctggt gcagaacatc      960
gaccaactct actccggcgg cggcaaggtg ggctacctcg tctacgcggg cggccggagg     1020
ttcctcttgg acctggagcg agatggttcg gtgggcattg ctggcttcgt gcccgcagga     1080
ggcgggacga gtgcgccctg cgccaccgg agccactgct tctatcgggg cacagtggac      1140
ggtagtcccc gctctctggc tgtctttgac ctctgtgggg gtctcgacgg cttcttcgcg     1200
gtcaagcacg cgcgctacac cctaaagcca ctgctgcgcg gaccctgggc ggaggaagaa     1260
aaggggcgcg tgtacgggga tgggtccgca cggatcctgc acgtctacac ccgcgagggc     1320
ttcagcttcg aggccctgcc gccgcgcgcc agctgcgaaa ccccccgcgtc cacaccggag    1380 gcccacgagc atgctccggc gcacagcaac ccgagcggac gcgcagcact ggcctcgcag     1440
ctcttggacc agtccgctct ctcgcccgct ggggctcag gaccgcagac gtggtggcgg      1500
cggcggcgcc gctccatctc ccgggcccgc caggtggagc tgcttctggt ggctgacgcg     1560
tccatggcgc ggttgtatgg ccggggcctg cagcattacc tgctgaccct ggcctccatc     1620
gccaataggc tgtacagcca tgctagcatc gagaaccaca tccgcctggc cgtggtgaag     1680
gtggtggtgc taggcgacaa ggacaagagc ctggaagtga gcaagaacgc tgccaccaca     1740
ctcaagaact tttgcaagtg gcagcaccaa cacaaccagc tgggagatga ccatgaggag     1800
cactacgatg cagctatcct gtttactcgg gaggatttat gtgggcatca ttcatgtgac     1860
accctgggaa tggcagacgt tgggaccata tgttctccag agcgcagctg tgctgtgatt     1920
gaagacgatg gcctccacgc agccttcact gtggctcacg aaatcggaca tttacttggc     1980
ctctcccatg acgattccaa attctgtgaa gagacctttg gttccacaga agataagcgc     2040
ttaatgtctt ccatccttac cagcattgat gcatctaagc cctggtccaa atgcacttca     2100
gccaccatca cagaattcct ggatgatggc catggtaact gtttgctgga cctaccacga     2160
aagcagatcc tgggccccga agaactccca ggacagacct acgatgccac ccagcagtgc     2220
aacctgacat tcgggcctga gtactccgtg tgtcccggca tggatgtctg tgctcgcctg     2280
tggtgtgctg tggtacgcca gggccagatg gtctgtctga ccaagaagct gcctgcggtg     2340
gaagggacgc cttgtggaaa ggggagaatc tgcctgcagg gcaaatgtgt ggacaaaacc     2400
aagaaaaaat attattcaac gtcaagccat ggcaactggg gatcttgggg atcctggggc     2460
cagtgttctc gctcatgtgg aggaggagtg cagtttgcct atcgtcactg taataaccct     2520
gctcccagaa caacggacg ctactgcaca gggaagaggg ccatctaccg ctcctgcagt      2580
ctcatgccct gcccacccaa tggtaaatca tttcgtcatg aacagtgtga ggccaaaaat     2640
ggctatcagt ctgatgcaaa aggagtcaaa acttttgtgg aatgggttcc caaatatgca     2700
ggtgtcctgc cagcggatgt gtgcaagctg acctgcagag ccaagggcac tggctactat     2760
gtggtatttt ctccaaaggt gaccgatggc actgaatgta ggctgtacag taattccgtc     2820
tgcgtccggg ggaagtgtgt gagaactggc tgtgacggca tcattggctc aaagctgcag     2880
```

```
tatgacaagt gcggagtatg tggaggagac aactccagct gtacaaagat tgttggaacc    2940
tttaataaga aaagtaaggg ttacactgac gtggtgagga ttcctgaagg ggcaacccac    3000
ataaaagttc gacagttcaa agccaaagac cagactagat tcactgccta tttagccctg    3060
aaaaagaaaa acggtgagta ccttatcaat ggaaagtaca tgatctccac ttcagagact    3120
atcattgaca tcaatggaac agtcatgaac tatagcggtt ggagccacag ggatgacttc    3180
ctgcatggca tgggctactc tgccacgaag gaaattctaa tagtgcagat tcttgcaaca    3240
gaccccacta aaccattaga tgtccgttat agcttttttg ttcccaagaa gtccactcca    3300
aaagtaaact ctgtcactag tcatggcagc aataaagtgg gatcacacac ttcgcagccg    3360
cagtgggtca cgggcccatg gctcgcctgc tctaggacct gtgacacagg ttggcacacc    3420
agaacggtgc agtgccagga tggaaaccgg aagttagcaa aaggatgtcc tctctcccaa    3480
aggccttctg cgtttaagca atgcttgttg aagaaatgtt agcctgtggt tatgatctta    3540
tgcacaaaga taactggagg attcagcact gatgcagtcg tggtgaacag gaggtctacc    3600
taacgcacag aaagtcatgc ttcagtgaca ttgtcaacag gagtccaatt atgggcagaa    3660
tctgctctct gtgaccaaaa gaggatgtgc actgcttcac gtgacagtgg tgaccttgca    3720
atatagaaaa acttgggagt tattgaacat cccctgggct tacaagaaac actgatgaat    3780
gtaaaatcag gggacatttg aagatggcag aactgtctcc cccttgtcac ctacctctga    3840
tagaatgtct ttaatggtat cataatcatt ttcacccata atacacagta gcttcttctt    3900
actgtttgta aatacattct cccttggtat gtcactttat atcccctggt tctattaaaa    3960
tatccatata tatttctata aaaaagtgt ttgaccaaag taggtctgca gctatttcaa     4020
cttccttccg tttccagaaa gagctgtgga tattttactg gaaattaaga acttgctgct    4080
gttttaataa gatgtagtat attttctgac tacaggagat aaaatttcag tcaaaaaacc    4140 atttttgacag caagtatctt ctgagaaatt ttgaaaagta aatagatctc agtgtatcta    4200
gtcacttaaa tacatacacg ggttcattta cttaaaccctt tgactgcctg tatttttttc    4260
aggtagctag ccaaattaat gcataatttc agatgtagaa gtagggtttg cgtgtgtgtg    4320
tgtgatcata ctcaagagtc taaaaactag tttccttgtg ttggaaattt aaaaggaaaa    4380
aaatcgtatt tcactgtgtt ttcaattat atttttcacaa ctactttctc tctccagagc    4440
tttcatctga tatctcacaa tgtatgatat acgtacaaaa cacacagcaa gttttctatc    4500
atgtccaaca cattcaacac tggtataccct cctaccagca agcctttaaa atgcatttgt    4560
gtttgcttat ttgttttgtt caagggttca gtaagaccta caatgttttg tatttcttga    4620
cttattttat tagaaacatt aaagatcact tggtagttag ccacattgag aagtggttat    4680
cattgttaat gtggttaatg ccaaaaagtg gttaatatta ataagactgt ttccacacca    4740
taggcaataa tttcttaatt taaaaaatct aagtatattc ctattgtact aaatattttt    4800
cccaactgga aagcacttga ttgtacccgt aagtgtttga gtgatgacat gtgatgattt    4860
tcagaaagtt gttgttttttg tttccatagc ctgtttaagt aggttgtaag tttgaatagt    4920
tagacatgga aattatttta taagcacaca cctaaagata tcttttttaga tgataaaatg    4980 tacaccccccc catcaccaac ctcacaactt agaaaatcta agttgtttga tttctttggg    5040
atttcttttg ttgtgaaaca ctgcaaagcc aattttttctt tataaaaatt catagtaatc    5100
ctgccaaatg tgcctattgt taaagatttg catgtgaaga tcttagggaa ccactgtttg    5160
agttctacaa gctcatgaga gtttatttttt attataagat gttttttaata taaaagaatt    5220
```

```
atgtaactga tcactatatt acatcatttc agtgggccag gaaaatagat gtcttgctgt    5280
tttcagtatt ttcttaagaa attgctttta aaacaaataa ttgttttaca aaaccaataa    5340
ttatcctttg aatttttcata gactgacttt gcttttgacg tagaaatttt ttttctcaat    5400
aaattatcac tttgagaaat gaggcctgta caaggctgat aacctatatg tgatggagat    5460
cacccaatgc caagggcaga aagcaaacct agttaaatag gtgagaaaaa aataataat    5520 cccagtgcca tttgtctgtg caaagagaat taggagagag gttaatgtta ctttttcca    5580 ttttggaaat aattttaatc aagtaactca aatgtgacaa aatttatttt tattttttgt    5640
ggttatattc ccaacaacat taaaaaatac tcgaggcata aatgtagttg tctcctactc    5700
tgcttctctt actatactca tacattttta atatggttta tcaatgattc atgtttccct    5760
caaatagtga tggtttacac ctgtcatgga aacaatccta gagagctcag agcaattaaa    5820
ccactattcc atgcttttaa gtagttttct ccaccttttt cttatgagtc tcactagatt    5880
gactgaggaa tgtatgtcta aattcctgga gaagatgata tggattggaa actgaaattc    5940
agagaaatgg agtgttcaat agataccacg aattgtgaac aaagggaaaa ttctatacaa    6000
ctcaatctaa gtcagtccac tttgacttcg tactgtcttt cacctttcca ttgttgcatc    6060 ttgaatttt taaaatgtct agaattcagg atgctagggg ctacttcttt aaaaaaaaaa    6120 aaaaaaaga attcgtctga aaatgctcag gtttgtaaga atctaatctc acttacataa    6180
ctaagcactc cataataagt tttattaagt acaaagggag ccagaaaaaa tgacattttat    6240 ttcttctaga tcagaaaaat ttaaattaag ccctgccttg ctgtttagaa atatgtgggc    6300
attgttataa tttattcaat aaatttatgt tcctttgcct tcctgtggaa acagtttat    6360 cccactaaac taggaattag gggataaatc acaaacaaaa aaaaagttgc agcactgaaa    6420
aaaagtaatt tattgttttt gcaactggta tgtgaatttg tgtgataaaa ttatttattc    6480
ttatttaaca aaaatatgtt caaattttc tatatttaaa atgttttgct gttgtcctac    6540
tttttaattt atgcttcatg tttgtgtata aagtacactt ttcactttg tgagtttaca    6600 taatatacag cactggttgc ttttgtattt ttttacagaa agctttctgt gtgaagcagg    6660
tgtatatgta tatattcctc atgtattctt attctgatac tatcattttt ctttccaagg    6720
aaattttaat ctgtcatgac caatagtgtt cattacttgt gcctatgata ataggtttt    6780 tacatcacat taacactatt ttttccaagt cacaaataag aaaaacactt attcaatgaa    6840
acaaggtgca agttttaaat ttgggtacac aaatagccta gaagcttcct acagacgcta    6900
agacacagcc aataatcaga tcctttcact tcatcgagaa acttggacaa gtcgatattg    6960
atgtattaga tgaaagttgt ctacacacaa cttctgaggg atacaaacga taataaaacc    7020
aaatgttgtc tgtttctcct ttagaaacac ctccctaaaat taatatcatt tagtctctag    7080
tgtctgtagg attctacaga tgagcacaaa tagattgggt ttgtataaca aatgctaata    7140
gtcataactg tttctacaaa tatggggtgt ccattaagag aatgtgatgt tttcctactg    7200
ctgttgaatc ccatggggtg attataggac ttgaaatagg cagagtcacc tctgatgaca    7260
tcagcttgcc tctgtgattt cacagtctga tcctggcaac aagacaaagc acccttggac    7320
acacagccaa tctctggttg tgatatttcc ccattgattc cttccttgtt aacaaggtca    7380
ttttaatggt tcaggtgagg acagcagcca gattcaaagt ccagaatttg tgctgttaca    7440
tagagttcac actgtcaaat aacattgaat ttaataatga tcaaattttt ctagtagtct    7500
ttggcagagt gtataatctc attggcatga ttggtgaata ttactaatct ctttataatg    7560
aaagatgctt tacaaatacc ttatatttgc taacatttca aaactactaa ataaatgaaa    7620
```

```
tagccatgtg tacagaaatg gtcatttaaa gctttaatag aaccaaattc aagacaatgt   7680
atcatttaga cacacagaaa aggaacttgt atgttttccc tattattttt ctcatttgcc   7740
aacaatctat agttttaggt tatcaaacag atagatcaac ttaactggct agtacattga   7800
aaaatcttcc taagaatcct ttgttagcat aatctataga gataatttct caaattatat   7860
catcatgatg catataaact ctataatgta taattgtgtt tcatttattt aatgtatgag   7920
aacatattga aatacaaaac catgcattag ccaaaaaatt ggaatacagg tagtgttcag   7980
atcagcaaaa cattcagtct ggtaaatgcc tgcctggggc tatgatatca ttctcaatgc   8040
aggttttatg gaaaaactaa agaatatgt  tgttagatga tgttggtttt gaaaaaaaaa   8100
agacattaac atacacatta gttagcccag ttaattgcat tctactaata tagttgcaca   8160
ttagcaataa ttttgctgtc tctggtcttt attttgtggc ttcaactaac tggaccatgt   8220
ggactgtaaa ggtcaaatgg aaaaaacgag cagtggcccc tcatcctgta aggtactgct   8280
acatcagagt gacctaaaag tctaacactg tgaggaaaac tgtgatttgt aggaaaaaaa   8340
aaaaaaacaa ataaaaaaca gggcatgctt tttaattttt ttccactttc ctttggcaca   8400
cccaatgaac aattctaatt tttattgagg tgctaacatc tttcgtgacc gactgtcaaa   8460 tgtggtatttt ttgagttact attttttctac atgattttac agtttgcaag aaagacctct   8520
aagctttgtg tcacggtagg gcacaacttg atactcaaaa tttgaaaaat aagcacatcc   8580
aatgattgtt ttgaccaaca gtggtcagtg acgtaaactg catgtgcatc tgaggacatt   8640
taaggggtca ttaaaatttg aggagcatca ggccggagta gcagactttt agatgagtca   8700
tatttcagca ttcactaagt cctcagcatt ccattcaaac tgtcgtgtat atttggcctg   8760
attttttttc aagctttgca ataatttatg ttattggtaa acacttggtg actatatctc   8820
agccttttct ttaacaactc acaatatatt agaaacacgt ctacctatac tgagagtata   8880
tttacaatag aagaacatac tgtatgtgac tttgtaaagc tagacttttg attaagaaat   8940
atataatctc tggatgctat ttttgcatta tacactcagg cacaacgtaa accttgatgg   9000
ctcatcttgc tacaattacg agttgaaaaa cactacttac gtatttgtat gacctattag   9060
tcagaggaaa tcatacatat gctttgtaaa tagactttgc agataactaa atagactgaa   9120
gaaatatgtt gcatttgata gaagcaattg cataaatatt tggtttctat attagagtct   9180
gtgagtaaag tcaagtaata aacctaagta ggtataacag attttaaac  cttgaaactt   9240 gctttgatgg tagagaaaat cattgaagat ttacatactg tatataagat gtaaaatgta   9300
cgctgcttat taccctcaat tttccagaag caatggtata taatgcagtt gaaaaaccaa   9360
aaatcttgga aaactaagac gggtcttgtt taaaatgtct ctcagctttg caaccttca    9420 aatcttaatc aactatttaa agcattactg tgtcttgtag cctgcattcc acaacagctc   9480
tgttattcag gtaaaagact tgaactgagc cgtttgggac ctatactgta atattttcat   9540
tgaggaacaa tatcctatttt tgtaaagcat ttccctatgt gtgactttaa actgtaaaat   9600
taaacactgc ttttgtgggt tcagtgggca taataaatat aaattgtaaa ctaggttaaa   9660
gta                                                                9663
```

<210> SEQ ID NO 17
<211> LENGTH: 930
<212> TYPE: PRT
<213> ORGANISM: Homo sapiens

<400> SEQUENCE: 17

```
Met Leu Leu Gly Trp Ala Ser Leu Leu Leu Cys Ala Phe Arg Leu Pro
1               5                   10                  15
Leu Ala Ala Val Gly Pro Ala Ala Thr Pro Ala Gln Asp Lys Ala Gly
            20                  25                  30
Gln Pro Pro Thr Ala Ala Ala Ala Gln Pro Arg Arg Arg Gln Gly
            35                  40                  45
Glu Glu Val Gln Glu Arg Ala Glu Pro Pro Gly His Pro His Pro Leu
50                  55                  60
Ala Gln Arg Arg Arg Ser Lys Gly Leu Val Gln Asn Ile Asp Gln Leu
65                  70                  75                  80
Tyr Ser Gly Gly Gly Lys Val Gly Tyr Leu Val Tyr Ala Gly Gly Arg
                85                  90                  95
Arg Phe Leu Leu Asp Leu Glu Arg Asp Gly Ser Val Gly Ile Ala Gly
            100                 105                 110
Phe Val Pro Ala Gly Gly Thr Ser Ala Pro Trp Arg His Arg Ser
            115                 120                 125
His Cys Phe Tyr Arg Gly Thr Val Asp Gly Ser Pro Arg Ser Leu Ala
        130                 135                 140
Val Phe Asp Leu Cys Gly Gly Leu Asp Gly Phe Phe Ala Val Lys His
145                 150                 155                 160
Ala Arg Tyr Thr Leu Lys Pro Leu Leu Arg Gly Pro Trp Ala Glu Glu
                165                 170                 175
Glu Lys Gly Arg Val Tyr Gly Asp Gly Ser Ala Arg Ile Leu His Val
            180                 185                 190
Tyr Thr Arg Glu Gly Phe Ser Phe Glu Ala Leu Pro Pro Arg Ala Ser
            195                 200                 205
Cys Glu Thr Pro Ala Ser Thr Pro Glu Ala His Glu His Ala Pro Ala
210                 215                 220
His Ser Asn Pro Ser Gly Arg Ala Ala Leu Ala Ser Gln Leu Leu Asp
225                 230                 235                 240
Gln Ser Ala Leu Ser Pro Ala Gly Gly Ser Gly Pro Gln Thr Trp Trp
                245                 250                 255
Arg Arg Arg Arg Arg Ser Ile Ser Arg Ala Arg Gln Val Glu Leu Leu
            260                 265                 270
Leu Val Ala Asp Ala Ser Met Ala Arg Leu Tyr Gly Arg Gly Leu Gln
            275                 280                 285
His Tyr Leu Leu Thr Leu Ala Ser Ile Ala Asn Arg Leu Tyr Ser His
    290                 295                 300
Ala Ser Ile Glu Asn His Ile Arg Leu Ala Val Val Lys Val Val Val
305                 310                 315                 320
Leu Gly Asp Lys Asp Lys Ser Leu Glu Val Ser Lys Asn Ala Ala Thr
                325                 330                 335
Thr Leu Lys Asn Phe Cys Lys Trp Gln His Gln His Asn Gln Leu Gly
            340                 345                 350
Asp Asp His Glu Glu His Tyr Asp Ala Ala Ile Leu Phe Thr Arg Glu
            355                 360                 365
Asp Leu Cys Gly His His Ser Cys Asp Thr Leu Gly Met Ala Asp Val
    370                 375                 380
Gly Thr Ile Cys Ser Pro Glu Arg Ser Cys Ala Val Ile Glu Asp Asp
385                 390                 395                 400
Gly Leu His Ala Ala Phe Thr Val Ala His Glu Ile Gly His Leu Leu
                405                 410                 415
Gly Leu Ser His Asp Asp Ser Lys Phe Cys Glu Glu Thr Phe Gly Ser
```

-continued

```
             420                 425                 430
Thr Glu Asp Lys Arg Leu Met Ser Ser Ile Leu Thr Ser Ile Asp Ala
         435                 440                 445
Ser Lys Pro Trp Ser Lys Cys Thr Ser Ala Thr Ile Thr Glu Phe Leu
         450                 455                 460
Asp Asp Gly His Gly Asn Cys Leu Leu Asp Leu Pro Arg Lys Gln Ile
465                 470                 475                 480
Leu Gly Pro Glu Glu Leu Pro Gly Gln Thr Tyr Asp Ala Thr Gln Gln
                 485                 490                 495
Cys Asn Leu Thr Phe Gly Pro Glu Tyr Ser Val Cys Pro Gly Met Asp
                 500                 505                 510
Val Cys Ala Arg Leu Trp Cys Ala Val Val Arg Gln Gly Gln Met Val
             515                 520                 525
Cys Leu Thr Lys Lys Leu Pro Ala Val Glu Gly Thr Pro Cys Gly Lys
         530                 535                 540
Gly Arg Ile Cys Leu Gln Gly Lys Cys Val Asp Lys Thr Lys Lys Lys
545                 550                 555                 560
Tyr Tyr Ser Thr Ser Ser His Gly Asn Trp Gly Ser Trp Gly Ser Trp
                 565                 570                 575
Gly Gln Cys Ser Arg Ser Cys Gly Gly Val Gln Phe Ala Tyr Arg
                 580                 585                 590
His Cys Asn Asn Pro Ala Pro Arg Asn Gly Arg Tyr Cys Thr Gly
             595                 600                 605
Lys Arg Ala Ile Tyr Arg Ser Cys Ser Leu Met Pro Cys Pro Pro Asn
         610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                 645                 650                 655
Ala Gly Val Leu Pro Ala Asp Val Cys Lys Leu Thr Cys Arg Ala Lys
                 660                 665                 670
Gly Thr Gly Tyr Tyr Val Val Phe Ser Pro Lys Val Thr Asp Gly Thr
             675                 680                 685
Glu Cys Arg Leu Tyr Ser Asn Ser Val Cys Val Arg Gly Lys Cys Val
         690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                 725                 730                 735
Thr Phe Asn Lys Lys Ser Lys Gly Tyr Thr Asp Val Val Arg Ile Pro
                 740                 745                 750
Glu Gly Ala Thr His Ile Lys Val Arg Gln Phe Lys Ala Lys Asp Gln
             755                 760                 765
Thr Arg Phe Thr Ala Tyr Leu Ala Leu Lys Lys Lys Asn Gly Glu Tyr
         770                 775                 780
Leu Ile Asn Gly Lys Tyr Met Ile Ser Thr Ser Glu Thr Ile Ile Asp
785                 790                 795                 800
Ile Asn Gly Thr Val Met Asn Tyr Ser Gly Trp Ser His Arg Asp Asp
                 805                 810                 815
Phe Leu His Gly Met Gly Tyr Ser Ala Thr Lys Glu Ile Leu Ile Val
                 820                 825                 830
Gln Ile Leu Ala Thr Asp Pro Thr Lys Pro Leu Asp Val Arg Tyr Ser
             835                 840                 845
```

Phe Phe Val Pro Lys Lys Ser Thr Pro Lys Val Asn Ser Val Thr Ser
                850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
                900                 905                 910

Cys Pro Leu Ser Gln Arg Pro Ser Ala Phe Lys Gln Cys Leu Leu Lys
                915                 920                 925

Lys Cys
    930

<210> SEQ ID NO 18
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 18

Ala Gly Gly Trp Gly Pro Trp Gly Pro Trp Gly Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 19

Gly Gly Trp Gly Pro Trp Gly Pro Trp Gly Asp Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 20

Gly Trp Gly Pro Trp Gly Pro Trp Gly Asp Cys Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 21

Trp Gly Pro Trp Gly Pro Trp Gly Asp Cys Ser Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 22

Gly Pro Trp Gly Pro Trp Gly Asp Cys Ser Arg Thr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 23

Pro Trp Gly Pro Trp Gly Asp Cys Ser Arg Thr Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 24

Trp Gly Pro Trp Gly Asp Cys Ser Arg Thr Cys Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 25

Gly Pro Trp Gly Asp Cys Ser Arg Thr Cys Gly Gly
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 26

Pro Trp Gly Asp Cys Ser Arg Thr Cys Gly Gly Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 27

Trp Gly Asp Cys Ser Arg Thr Cys Gly Gly Gly Val
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 28

```
Gly Asp Cys Ser Arg Thr Cys Gly Gly Gly Val Gln
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 29

Asp Cys Ser Arg Thr Cys Gly Gly Gly Val Gln Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 30

Cys Ser Arg Thr Cys Gly Gly Gly Val Gln Phe Ser
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 31

Ser Arg Thr Cys Gly Gly Gly Val Gln Phe Ser Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 32

Arg Thr Cys Gly Gly Gly Val Gln Phe Ser Ser Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 33

Thr Cys Gly Gly Gly Val Gln Phe Ser Ser Arg Asp
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 34
```

```
Cys Gly Gly Gly Val Gln Phe Ser Ser Arg Asp Cys
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 35

```
Gly Gly Gly Val Gln Phe Ser Ser Arg Asp Cys Thr
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 36

```
Gly Gly Val Gln Phe Ser Ser Arg Asp Cys Thr Arg
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 37

```
Gly Val Gln Phe Ser Ser Arg Asp Cys Thr Arg Pro
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 38

```
Val Gln Phe Ser Ser Arg Asp Cys Thr Arg Pro Val
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 39

```
Gln Phe Ser Ser Arg Asp Cys Thr Arg Pro Val Pro
1               5                   10
```

<210> SEQ ID NO 40
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 40

```
Phe Ser Ser Arg Asp Cys Thr Arg Pro Val Pro Arg
```

<210> SEQ ID NO 41
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 41

Ser Ser Arg Asp Cys Thr Arg Pro Val Pro Arg Asn
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 42

Ser Arg Asp Cys Thr Arg Pro Val Pro Arg Asn Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 43

Arg Asp Cys Thr Arg Pro Val Pro Arg Asn Gly Gly
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 44

Asp Cys Thr Arg Pro Val Pro Arg Asn Gly Gly Lys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 45

Cys Thr Arg Pro Val Pro Arg Asn Gly Gly Lys Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 46

Thr Arg Pro Val Pro Arg Asn Gly Gly Lys Tyr Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 47

Arg Pro Val Pro Arg Asn Gly Gly Lys Tyr Cys Glu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 48

Pro Val Pro Arg Asn Gly Gly Lys Tyr Cys Glu Gly
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 49

Val Pro Arg Asn Gly Gly Lys Tyr Cys Glu Gly Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 50

Pro Arg Asn Gly Gly Lys Tyr Cys Glu Gly Arg Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 51

Arg Asn Gly Gly Lys Tyr Cys Glu Gly Arg Arg Thr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 52

Asn Gly Gly Lys Tyr Cys Glu Gly Arg Arg Thr Arg
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 53

Cys Glu Gly Arg Arg Thr Arg Phe Arg Ser Cys Asn
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 54

Glu Gly Arg Arg Thr Arg Phe Arg Ser Cys Asn Thr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 55

Gly Arg Arg Thr Arg Phe Arg Ser Cys Asn Thr Glu
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 56

Arg Arg Thr Arg Phe Arg Ser Cys Asn Thr Glu Asp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 57

Arg Thr Arg Phe Arg Ser Cys Asn Thr Glu Asp Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 58

Thr Arg Phe Arg Ser Cys Asn Thr Glu Asp Cys Pro
1               5                   10